US011317884B2

(12) United States Patent
Vancamberg et al.

(10) Patent No.: US 11,317,884 B2
(45) Date of Patent: May 3, 2022

(54) METHODS AND SYSTEMS FOR MAMMOGRAPHY AND BIOPSY WORKFLOW OPTIMIZATION

(71) Applicant: GE Precision Healthcare LLC, Milwaukee, WI (US)

(72) Inventors: Laurence Vancamberg, Poissy (FR); Serge Muller, Guyancourt (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 261 days.

(21) Appl. No.: 16/723,429

(22) Filed: Dec. 20, 2019

(65) Prior Publication Data
US 2021/0186450 A1   Jun. 24, 2021

(51) Int. Cl.
*A61B 6/00* (2006.01)
*A61B 6/02* (2006.01)
*G06T 7/00* (2017.01)

(52) U.S. Cl.
CPC ............ *A61B 6/5211* (2013.01); *A61B 6/025* (2013.01); *A61B 6/502* (2013.01); *A61B 6/584* (2013.01); *G06T 7/0012* (2013.01); *G06T 2200/24* (2013.01); *G06T 2207/30068* (2013.01)

(58) Field of Classification Search
CPC ....... A61B 6/025; A61B 6/0414; A61B 6/502; A61B 6/0091; A61B 6/0435; A61B 6/547; A61B 6/584
See application file for complete search history.

(56) References Cited

U.S. PATENT DOCUMENTS

| 5,164,998 | A | 11/1992 | Reinsch |
| 9,524,582 | B2 | 12/2016 | Ma et al. |
| 9,633,435 | B2 | 4/2017 | Ma et al. |
| 9,659,409 | B2 | 5/2017 | Siebarth et al. |
| 9,665,936 | B2 | 5/2017 | Kluckner et al. |
| 9,710,141 | B2 | 7/2017 | Braun et al. |
| 9,898,858 | B2 | 2/2018 | Tamersoy et al. |
| 9,962,138 | B2 | 5/2018 | Schweizer |
| 2005/0265516 | A1 | 12/2005 | Haider |
| 2009/0112119 | A1* | 4/2009 | Kim ................... A61B 10/0275 600/564 |
| 2011/0224904 | A1 | 9/2011 | Feiten et al. |
| 2015/0062301 | A1 | 3/2015 | Lin et al. |
| 2016/0128666 | A1 | 5/2016 | Grasruck et al. |
| 2016/0203265 | A1 | 7/2016 | Hardie et al. |
| 2016/0235386 | A1 | 8/2016 | Schweizer |
| 2016/0262713 | A1 | 9/2016 | Flohr et al. |

(Continued)

FOREIGN PATENT DOCUMENTS

WO    2018075053 A1    4/2018

*Primary Examiner* — Dani Fox
(74) *Attorney, Agent, or Firm* — McCoy Russell LLP

(57) ABSTRACT

Various methods and systems are provided for workflow monitoring during x-ray mammography and related procedures. In one example, a vision system is utilized to monitor an x-ray mammography system, accessories associated with the system, and surrounding environment. Based on the detection and user indications, via a user interface for example, one or more of a current mode of operation of the x-ray system, a current workflow step in the current mode, and one or more errors may be identified using the vision system, and one or more of indications to the user and system adjustments may be performed based on the identification.

20 Claims, 13 Drawing Sheets

(56) References Cited

U.S. PATENT DOCUMENTS

| | | |
|---|---|---|
| 2016/0267327 A1 | 9/2016 | Franz et al. |
| 2016/0296185 A1 | 10/2016 | Gemmel et al. |
| 2016/0367169 A1 | 12/2016 | Hardie et al. |
| 2016/0377545 A1 | 12/2016 | Wang |
| 2017/0000446 A1 | 1/2017 | Brinker et al. |
| 2017/0200317 A1 | 7/2017 | Hannemann et al. |
| 2017/0202544 A1 | 7/2017 | Vancamberg et al. |
| 2017/0224298 A1 | 8/2017 | Hannemann et al. |
| 2017/0354385 A1 | 12/2017 | Lerch |
| 2018/0063386 A1 | 3/2018 | Sharma et al. |
| 2018/0168523 A1 | 6/2018 | Vancamberg et al. |
| 2018/0235566 A1 | 8/2018 | Tamersoy et al. |
| 2018/0330496 A1 | 11/2018 | Ma et al. |
| 2018/0338742 A1 | 11/2018 | Singh et al. |

\* cited by examiner

METHODS AND SYSTEMS FOR MAMMOGRAPHY AND BIOPSY WORKFLOW OPTIMIZATION

FIELD

Embodiments of the subject matter disclosed herein relate to mammography and biopsy procedures, and more particularly, to workflow management during mammography and breast biopsy procedures.

BACKGROUND

Mammography is a medical imaging procedure for detecting one or more tumors of a breast. Based on mammography imaging, a breast biopsy procedure may be performed to obtain a biopsy sample of the concerned breast tissue for further analysis. In many breast biopsy procedures, a needle is inserted into the breast manually or by using an automatic needle guidance system. Both mammography and biopsy procedures may be performed using an x-ray mammography system, and involve specific workflow steps and accessories depending on the type of procedure performed.

BRIEF DESCRIPTION

In one embodiment, a method for an x-ray mammography system comprises: detecting, via vision sensing using one or more cameras coupled to the mammography system, one or more accessories coupled to the x-ray system; and automatically adjusting one or more inputs into a user interface of the mammography system based on the one or more accessories detected; wherein the one or more accessories includes a biopsy device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1A:
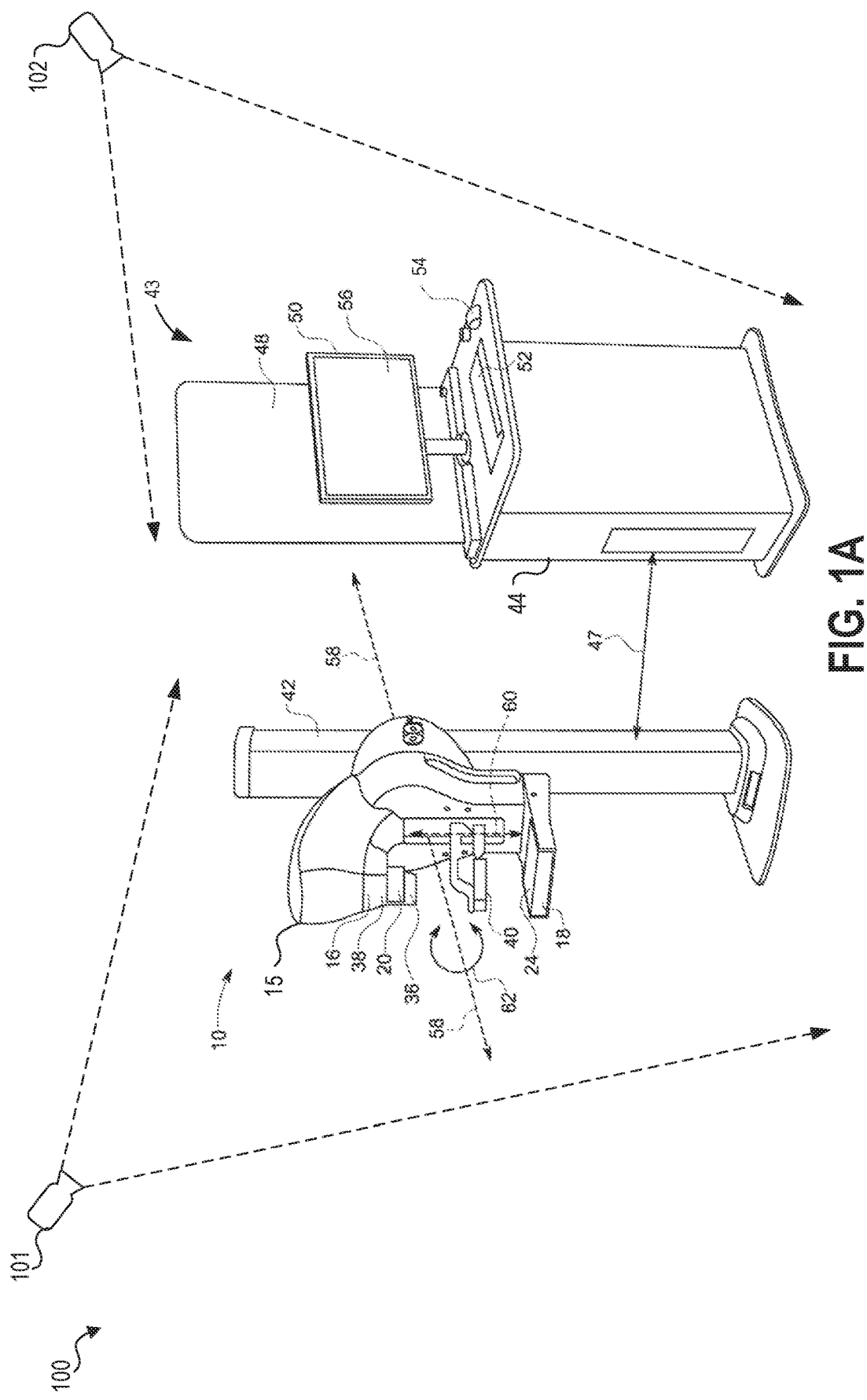
FIG. 1A is a schematic illustration of a mammography system including a vision sensing system, according to an embodiment of the disclosure.
Figure 1B:
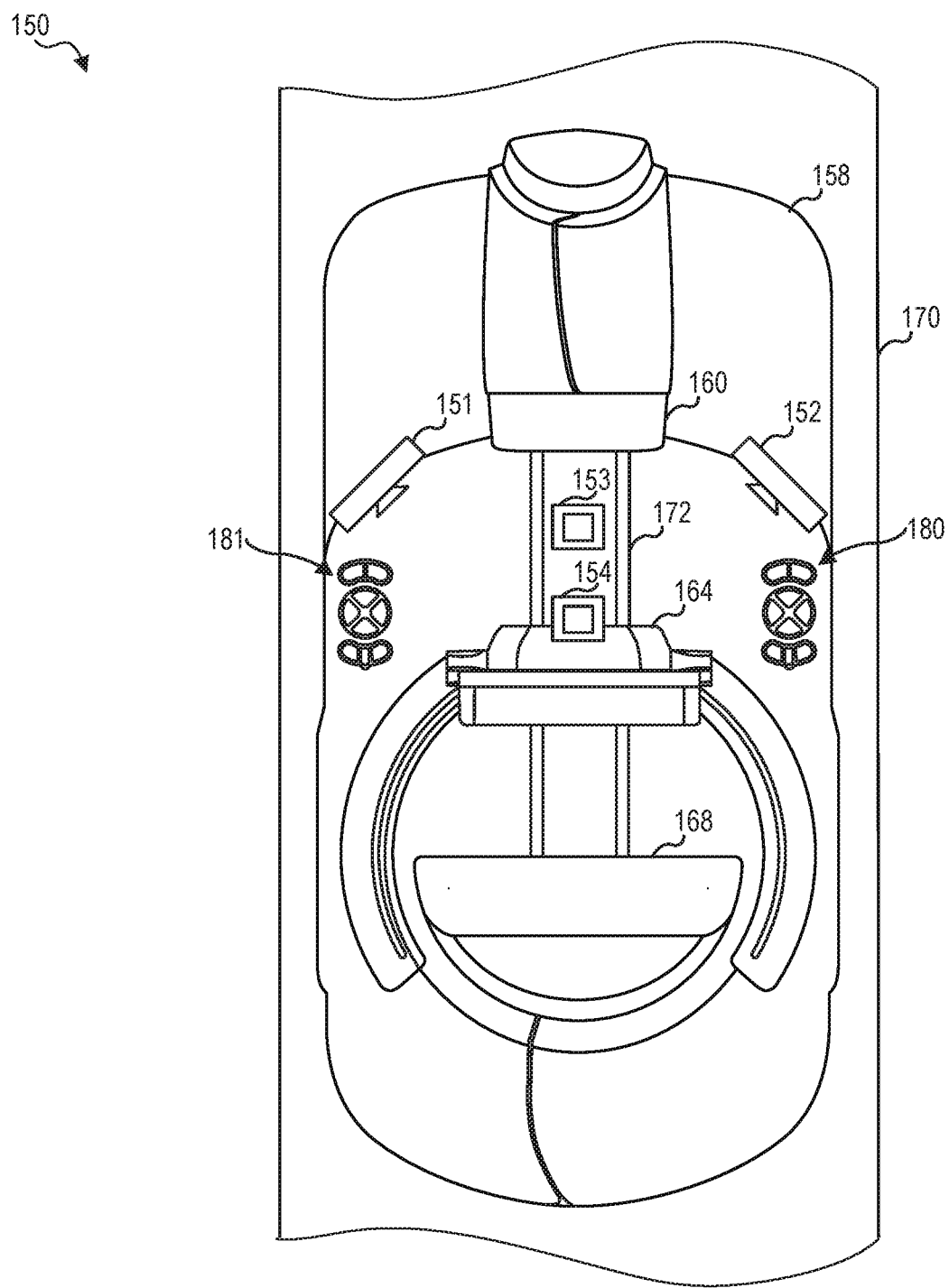
FIG. 1B is a schematic illustration of positioning of one or more cameras of a vision sensing system coupled to an x-ray system of a mammography system, according to an embodiment of the disclosure.
Figure 2:
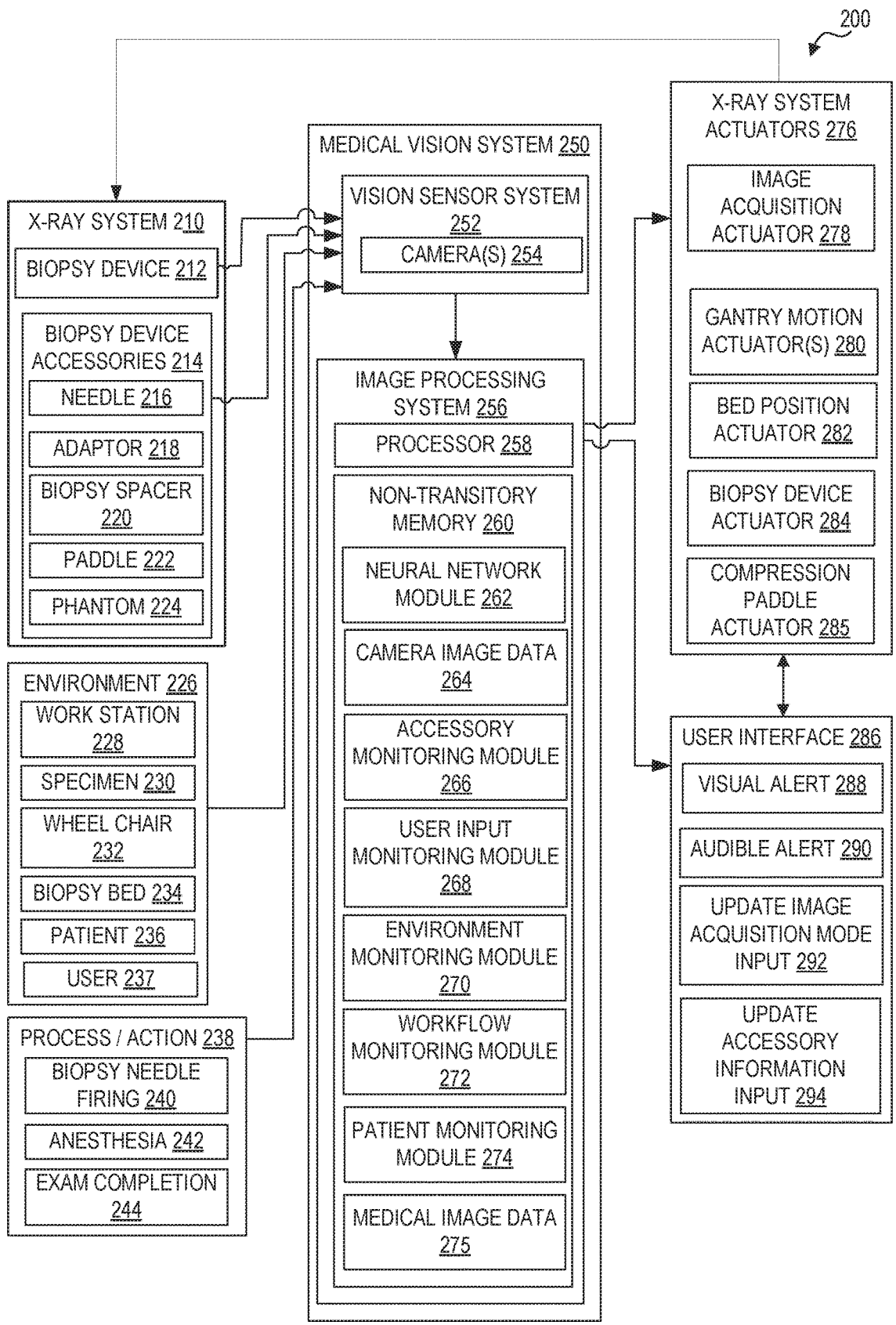
FIG. 2 is block diagram of a mammography system including a vision monitoring system, illustrating a plurality of objects sensed by the vision system and a plurality of actuators controlled based on the objects sensed, according to an embodiment of the disclosure.
Figure 4A:
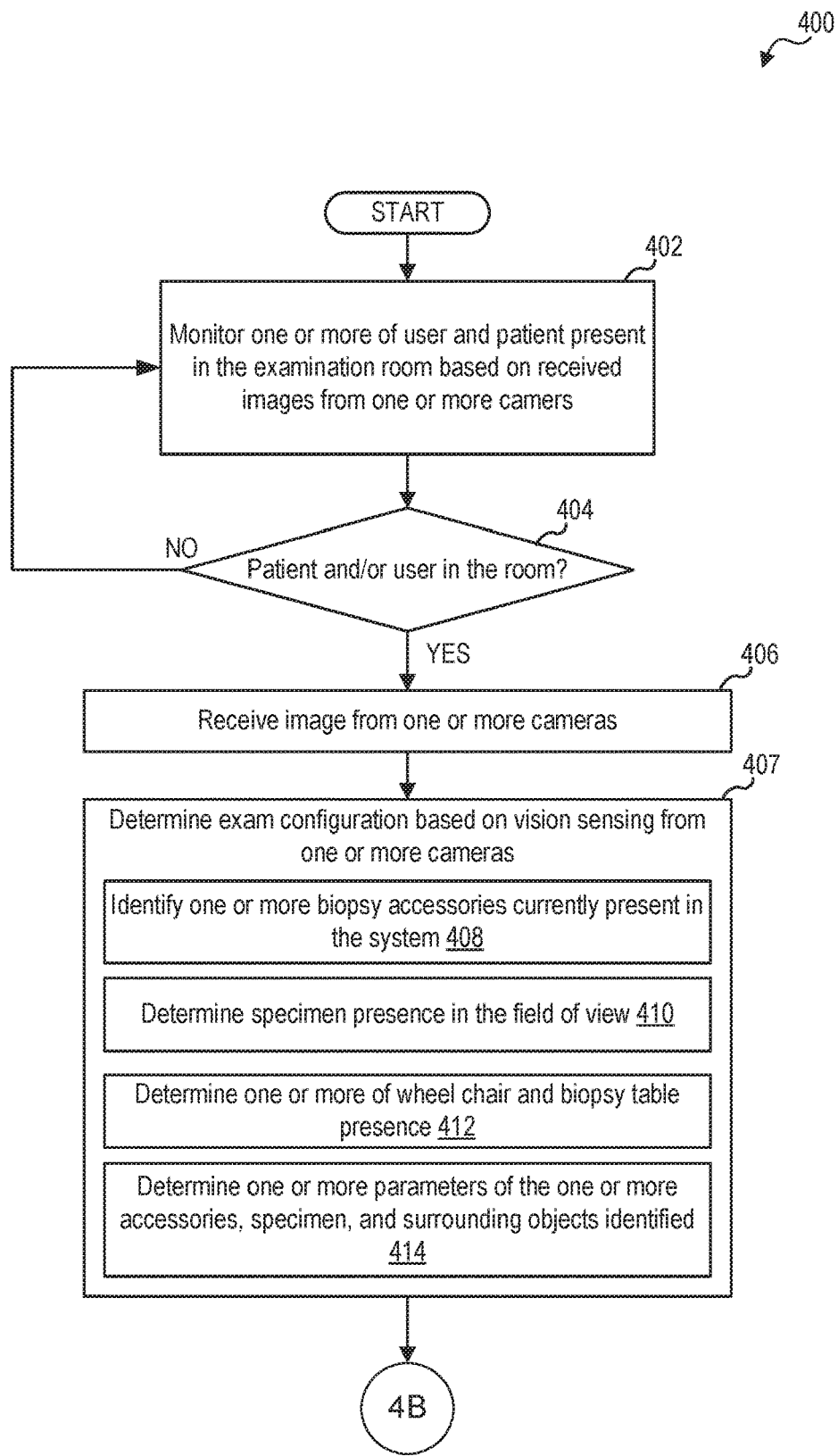
FIG. 4A is a high-level flow chart illustrating a method for detecting, with a vision system, one or more of accessories, specimen, and surrounding objects of a mammography system, and setting up the mammography system based on the monitoring, according to an embodiment of the disclosure.
Figure 4B:
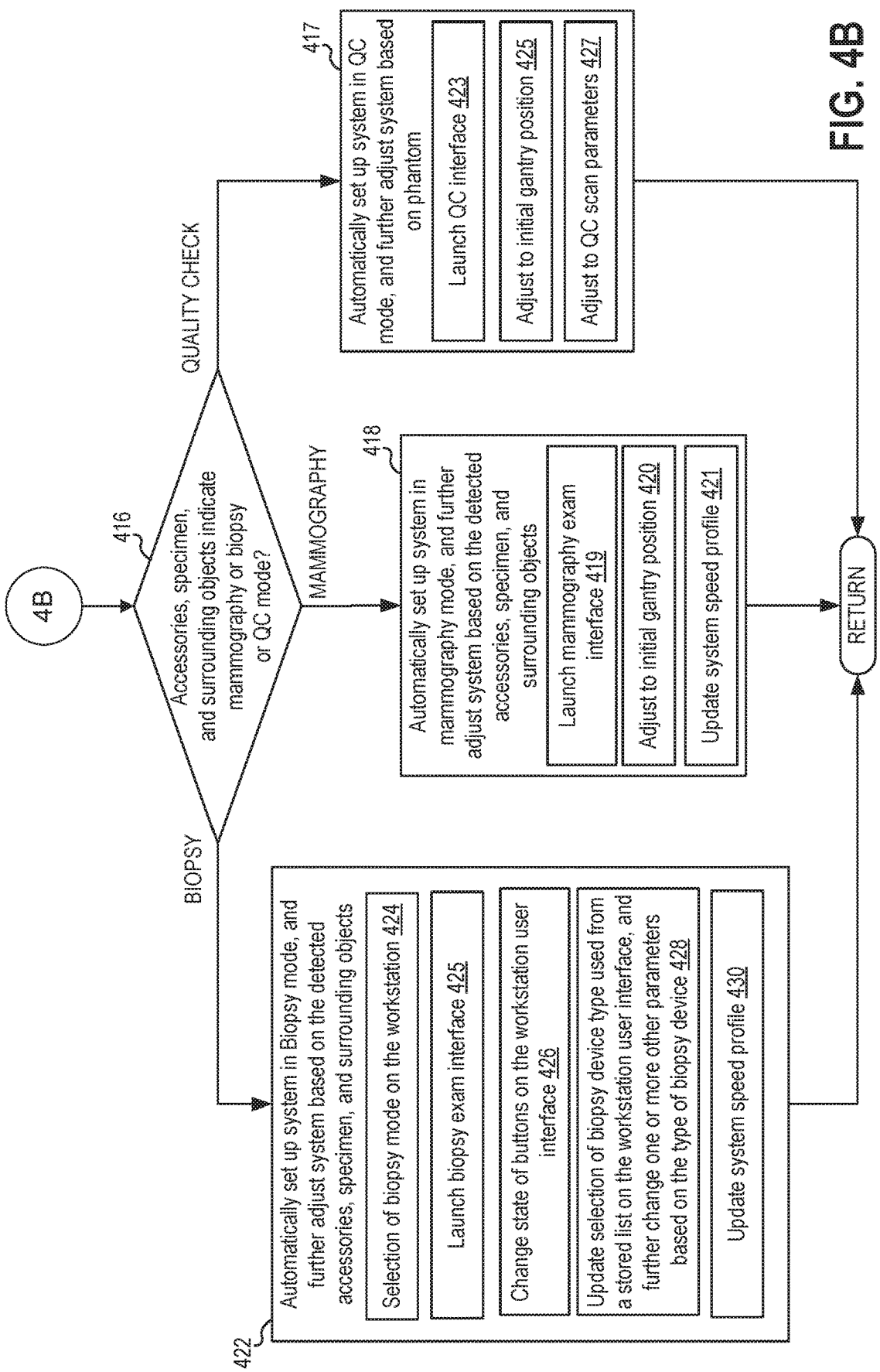
FIG. 4B is a continuation of FIG. 4A.
Figure 5A:
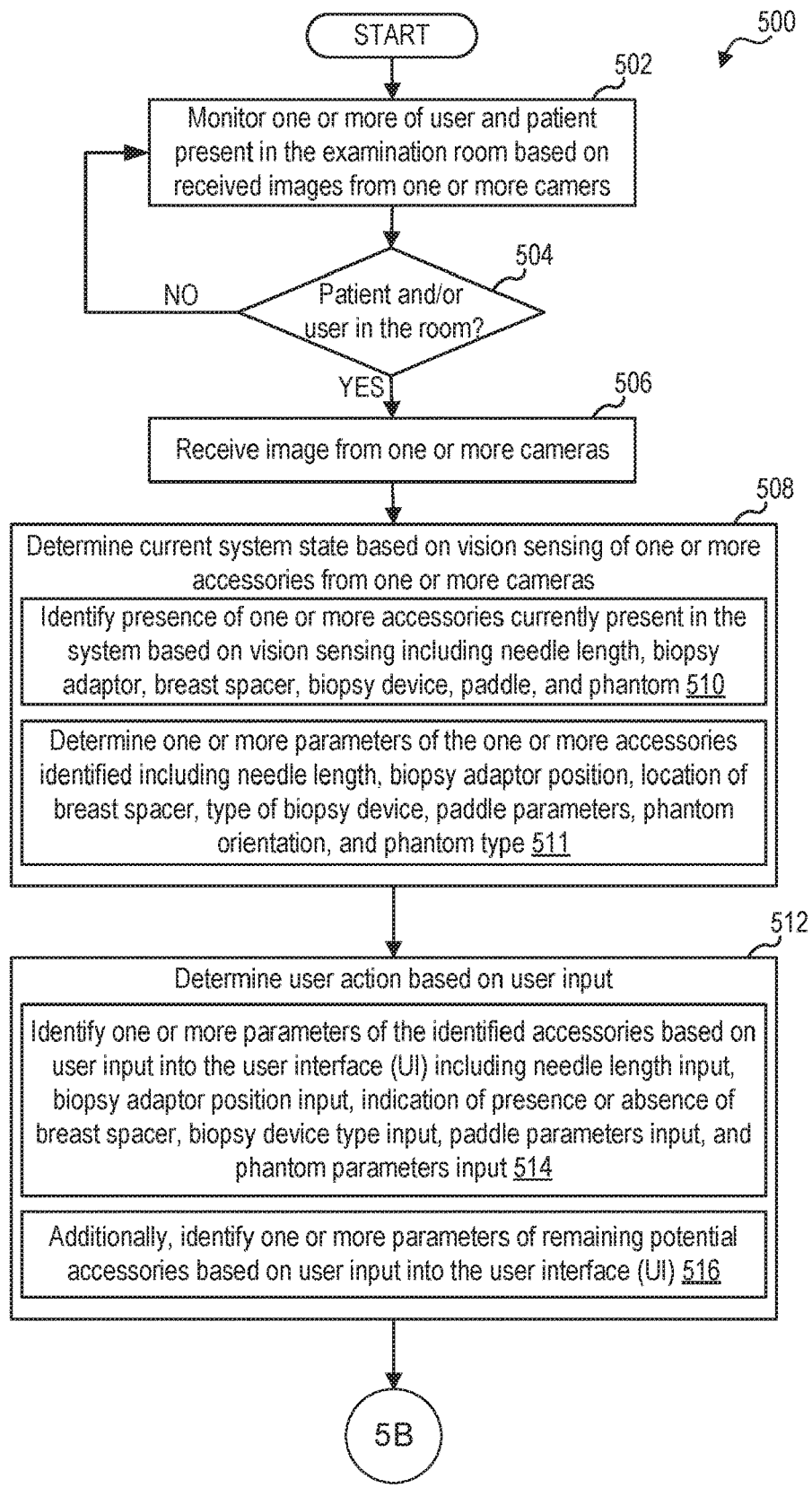
FIG. 5A is a high-level flow chart illustrating a method for detecting, with a vision system, one or more inconsistencies between a user action and an actual system set-up of a mammography system, and automatically controlling the mammography system, according to an embodiment of the disclosure.
Figure 5B:
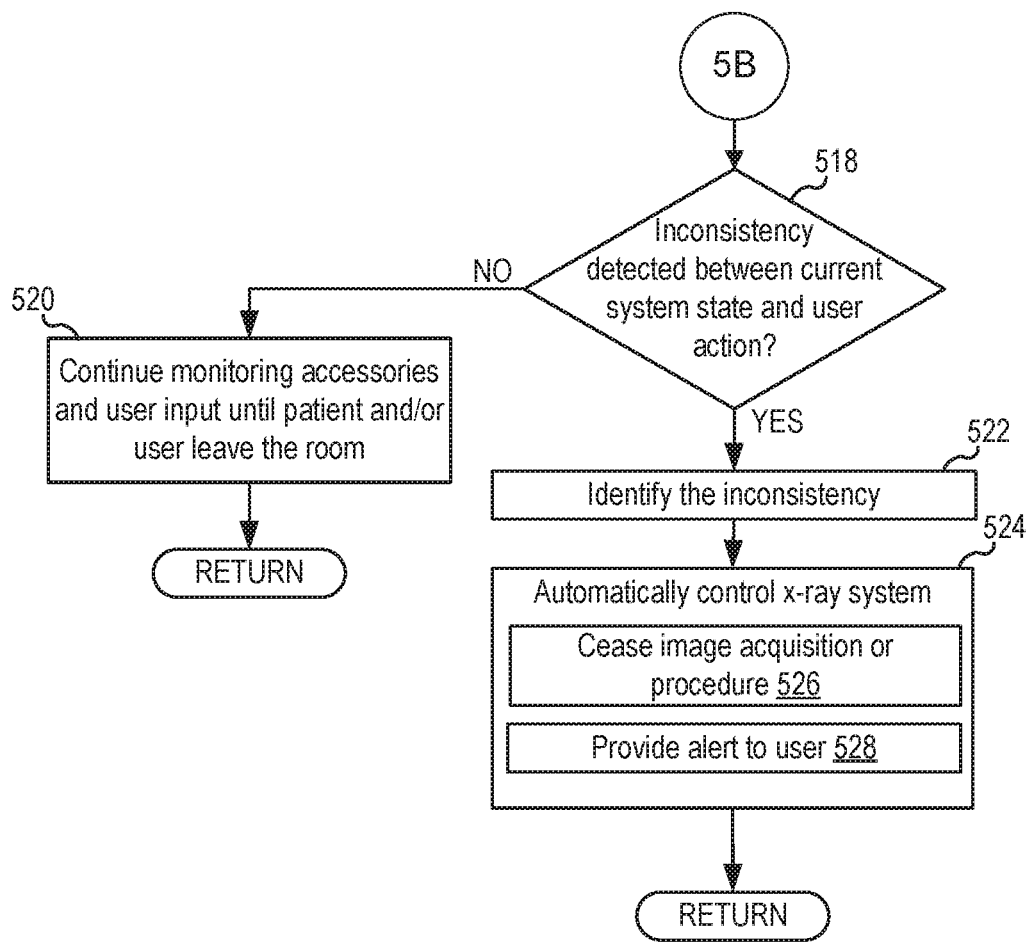
FIG. 5B is a continuation of FIG. 5A.
Figure 6A:
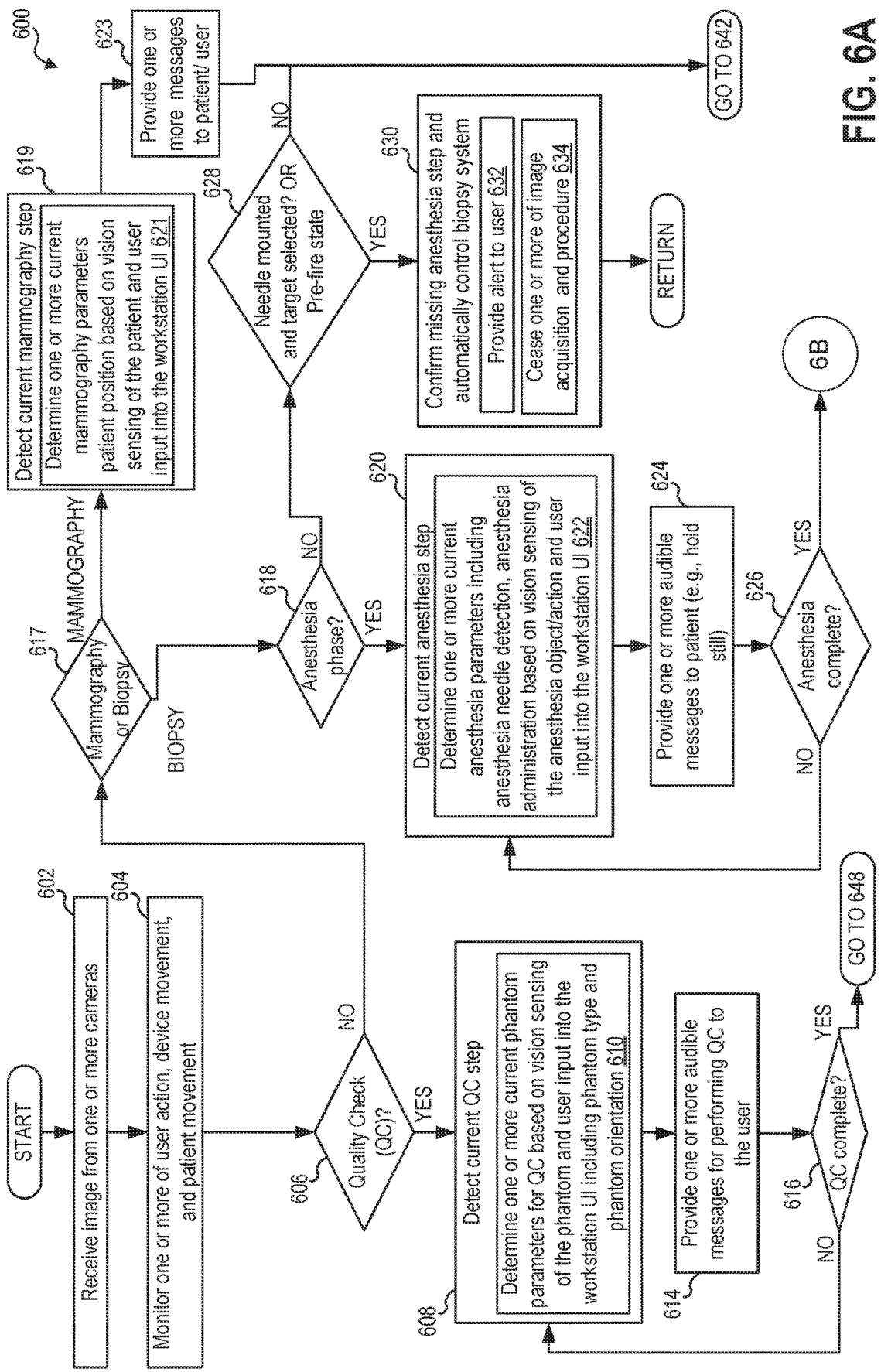
FIG. 6A is a high-level flow chart illustrating a method for detecting a workflow step in a procedure performed with a mammography system, and automatically adjusting one or more actions based on the workflow step, according to an embodiment of the disclosure.
Figure 6B:
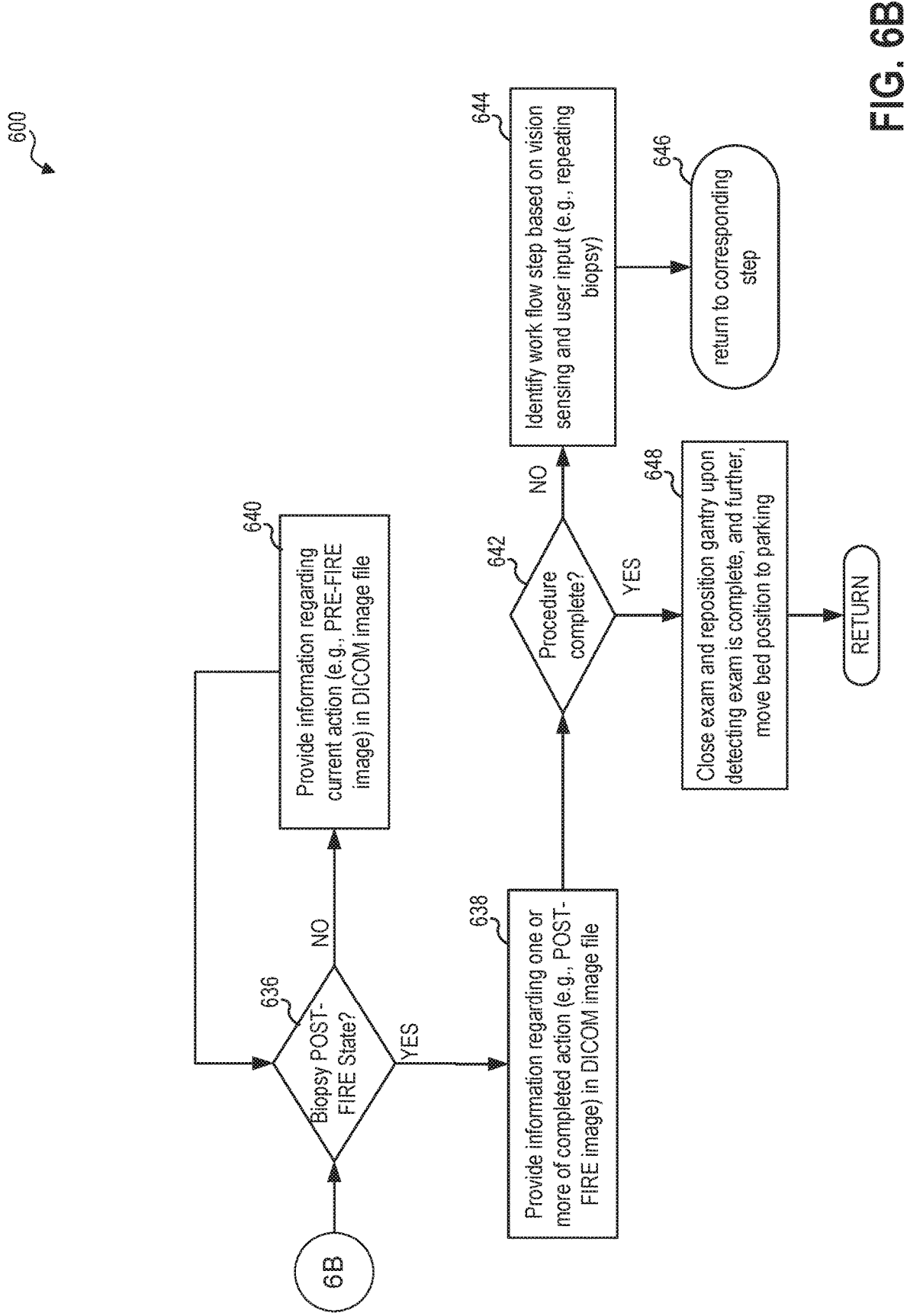
FIG. 6B is a continuation of FIG. 6A.
Figure 7:
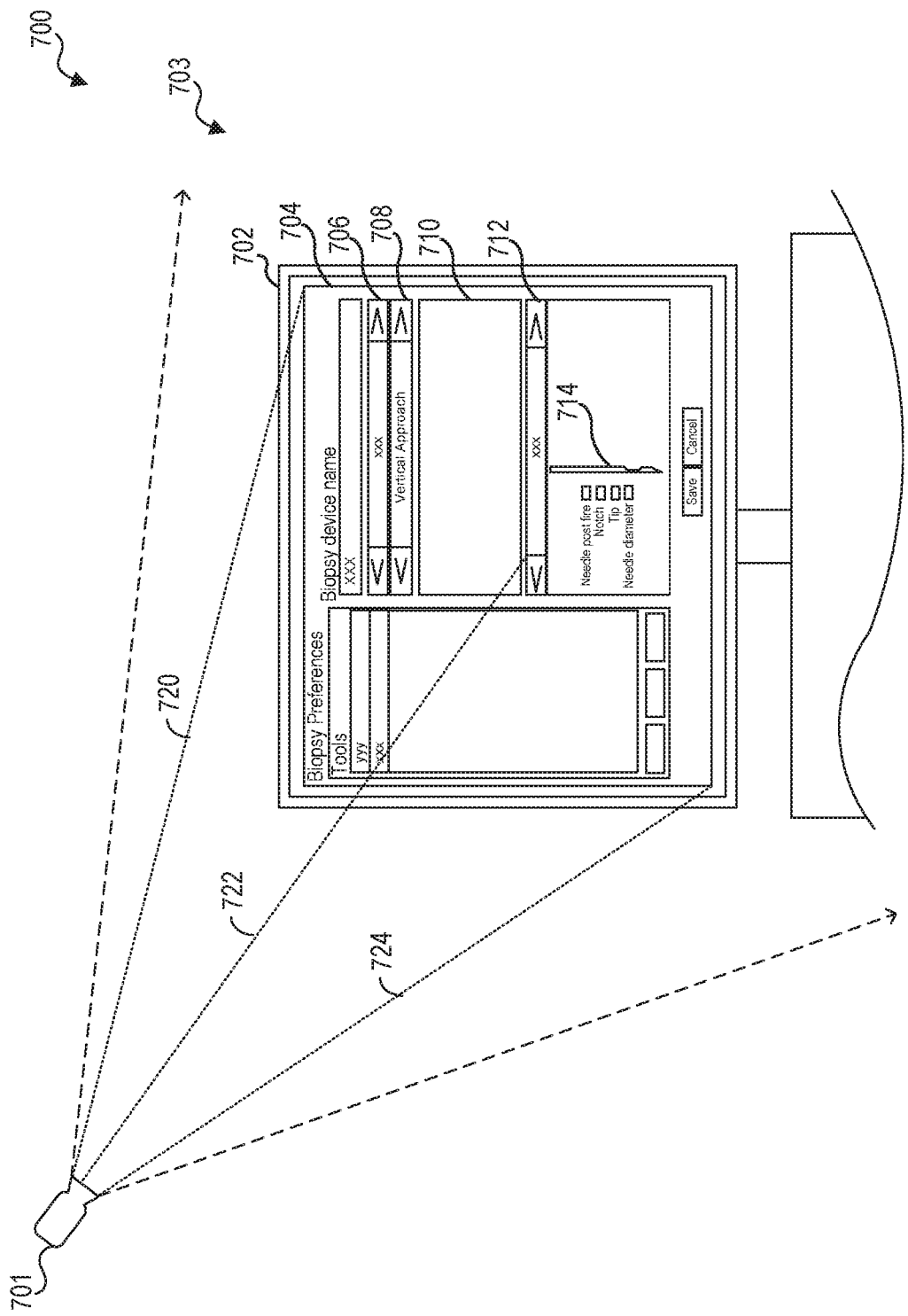
FIG. 7 is a schematic illustration of detecting user input from a user interface, via a vision system, according to an embodiment of the disclosure.
Figure 8:
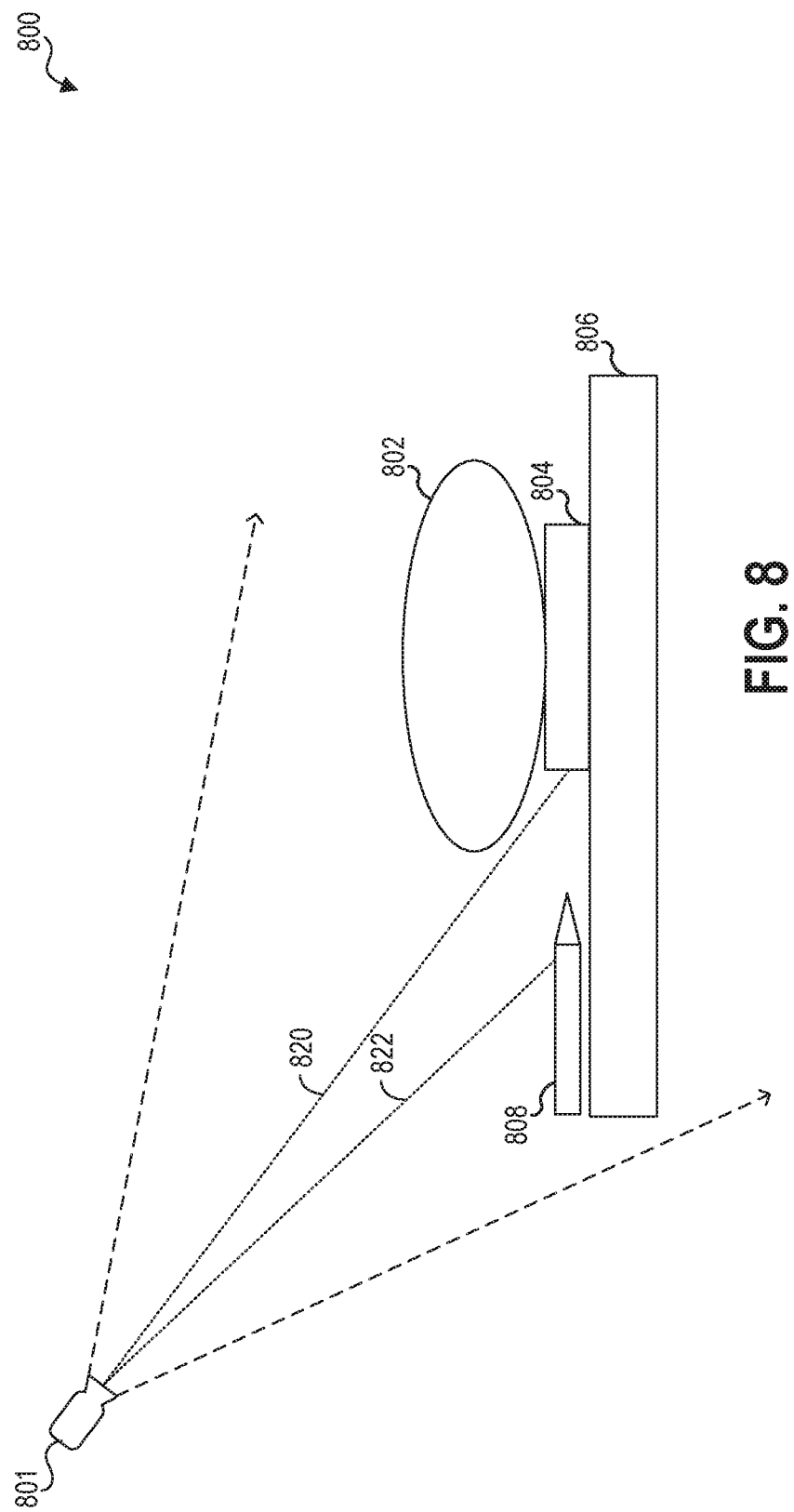
FIG. 8 is a schematic illustration of detecting, via a vision system, an accessory of a mammography system, according to an embodiment of the disclosure.

The following description relates to various embodiments for an x-ray system for mammography and biopsy procedures. An exemplary embodiment of an x-ray system is shown at FIG. 1A, which includes a vision system, including one or more cameras, to detect one or more of accessories associated with each procedure, the body part involved in the procedure, one or more objects in the environment surrounding the system, a user interface of the system, a patient, and a user. Based on the detection, the x-ray system including the vision system, may determine an intended procedure to be performed, inconsistencies due to user error, and a workflow step and take one or more actions accordingly, which may include one or more of controlling the system operation and/or set-up, providing one or more of an audible and a visual alert, and providing audible instructions based on the procedure performed. An exemplary embodiment of the vision system is illustrated at FIG. 1B including one or more cameras coupled to the x-ray system. A block diagram of one or more objects and actions detected by the vision system and one or more actuators of the x-ray system adjusted based on the one or more objects and actions detected is illustrated at FIG. 2. Further, an exemplary embodiment of the x-ray system within an examination area is shown FIG. 3. X-ray systems include plurality of accessories, and including a hardware sensor for each of the accessories can be time consuming and expensive. By using a vision system, any of the plurality of accessories associated with the x-ray system can be detected without additional hardware, and further, when a new accessory or a different accessory is included, a control system of the x-ray system may be easily configured to the enable monitoring of the additional accessories. An example method for detecting the accessories and setting up the system to perform either mammography or biopsy or quality check based on the accessories detected is shown at FIGS. 4A and 4B. Further, vision systems can be used to detect user error as illustrated at FIGS. 5A and 5B. Furthermore, the vision systems not only enable object monitoring, actions monitoring can be combined with object monitoring to detect a specific workflow step and control the x-ray system accordingly. Further still, a missing workflow step may be detected. An example use of the vision system in workflow monitoring and optimization is shown at FIGS. 6A and 6B. Example schematic illustrations of accessory monitoring are shown at FIGS. 7 and 8. An exemplary workflow sequence for quality control, mammography, and biopsy procedures using the mammography system and the vision system is discussed at FIG. 9.

Referring to FIG. 1, a mammography system 100 including an x-ray system 10 for performing a mammography procedure is shown, according to an exemplary embodiment. The x-ray system 10 may be a tomosynthesis system, such as a digital breast tomosynthesis ("DBT") system. Further, the x-ray system 10 may be used to perform one or more procedures including digital tomosynthesis imaging, and DBT guided breast biopsy.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation of the gantry 15 housing the radiation source 16 indicates a rotation up to a desired degree on either directions about the axis 58. For example, the angular range of rotation of the radiation source 16 may be $-\theta$ to $+\theta$, where $\theta$ may be such that the angular range is a limited angle range, less than 360 degrees. An exemplary x-ray system may have an angular range of ±11 degrees, which may allow rotation of the gantry (that is rotation of the radiation source) from −11 degrees to +11 degrees about an axis of rotation of the gantry. The angular range may vary depending on the manufacturing specifications. For example, the angular range for DBT systems may be approximately ±11 degrees to ±60 degrees, depending on the manufacturing specifications.

The radiation source 16 is directed toward a volume or object to be imaged, and is configured to emit radiation rays at desired times and to acquire one or more images. The radiation detector 18 is configured to receive the radiation rays via a surface 24. The detector 18 may be any one of a variety of different detectors, such as an x-ray detector, digital radiography detector, or flat panel detector. The collimator 20 is disposed adjacent to the radiation source 16 and is configured to adjust an irradiated zone of a subject.

In some exemplary embodiments, the system 10 may further include a patient shield 36 mounted to the radiation source 16 via face shield rails 38 such that a patient's body part (e.g., head) is not directly under the radiation. The system 10 may further include a compression paddle 40, which may be movable upward and downward in relation to the support structure along a vertical axis 60. Thus, the compression paddle 40 may be adjusted to be positioned closer to the radiation detector 18 by moving the compression paddle 40 downward toward the detector 18, and a distance between the detector 18 and the compression paddle 40 may be increased by moving the compression paddle upward along the vertical axis 60 away from the detector. The movement of the compression paddle 40 may be adjusted by a user via compression paddle actuator (not shown) included in the x-ray system 10. The compression paddle 40 may hold a body part, such as a breast, in place against the surface 24 of the radiation detector 18. The compression paddle 40 may compress the body part, and hold the body part still in place while optionally providing apertures to allow for insertion of a biopsy needle, such as a core needle, or a vacuum assisted core needle. In this way, compression paddle 40 may be utilized to compress the body part to minimize the thickness traversed by the x-rays and to help reduce movement of the body part due to the patient moving. The x-ray system 10 may also include an object support (not shown) on which the body part may be positioned.

The mammography system 100 may further include workstation 43 comprising a controller 44 including at least one processor and a memory. The controller 44 may be communicatively coupled to one or more components of the x-ray system 10 including one or more of the radiation source 16, radiation detector 18, the compression paddle 40, and a biopsy device. In one exemplary embodiment, the communication between the controller and the x-ray system 10 may be via a wireless communication system. In other exemplary embodiments, the controller 44 may be in electrical communication with the one or more components of the x-ray system via a cable 47. Further, in an exemplary embodiment, as shown in FIG. 1A, the controller 44 is integrated into workstation 43. In other exemplary embodiments, the controller 44 may be integrated into one or more of the various components of the system 10 disclosed above. Further, the controller 44 may include processing circuitry that executes stored program logic and may be any one of a different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a display 50, a keyboard 52, mouse 54, and/or other appropriate user input devices that facilitate control of the system 10 via a user interface 56.

Through its processors and controllers, the controller 44 may adjust the operation and function of the x-ray system 10. As an example, the controller 44 may provide timing control, as to when the x-ray source 16 emits x-rays, and may further adjust how the detector 18 reads and conveys information or signals after the x-rays hit the detector 18, and how the x-ray source 16 and the detector 18 move relative to one another and relative to the body part. The controller 44 may also control how information, including images 42 and data acquired during the operation, is processed, displayed, stored, and manipulated. The different processing steps, including receiving one or more signals from one or more sensors, receiving user input, evaluating the received signals/input, image processing, determining reconstruction error, outputting operation parameters including error indications, adjusting one or more actuators of the x-ray system to control operation of the x-ray system, performed by the controller 44, may be provided by a set of instructions stored in non-transitory memory of the processor. Information may also be stored in one or more non-transitory memories of controller 44 for later retrieval and use.

Further, as stated above, the radiation detector 18 receives the radiation rays 22 emitted by the radiation source 16. In particular, during imaging with the x-ray system, a projection image of the imaging body part may be obtained at the detector 18. In some exemplary embodiments, data, such as projection image data, received by the radiation detector 18 may be electrically and/or wirelessly communicated to the controller 44 from the radiation detector 18. The controller 44 may then reconstruct one or more scan images based on the projection image data, by implementing a reconstruction algorithm, for example. The reconstructed image may be displayed to the user on the user interface 50 via a display screen 56.

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the detector 18 and the compression paddle 40. Thus, a volume of the x-ray system 10 between the compression paddle 40 and the detector 18 is an imaging volume. The radiation source 16 then emits radiation rays on to the compressed breast, and a projection image of the breast is formed on the detector 18. The projection image may then be reconstructed by the controller 44, and displayed on the interface 50. During mammography, the gantry 15 may be adjusted at different angles to obtain images at different orientations, such as a cranio-caudal (CC) image and a medio-lateral oblique (MLO) image. In one example, the gantry 15 may be rotated about the axis 58 while the compression paddle 40 and the detector 18 remain stationary. In other examples, the gantry 15, the compression paddle 40, and the detector 18 may be rotated as a single unit about the axis 58.

Further, the x-ray system 10 may be operated in a tomosynthesis mode for performing digital breast tomosynthesis (DBT). During tomosynthesis, the x-ray system 10 may be operated to direct low-dose radiation towards the imaging volume (between the compression paddle 40 and the detector 18) at various angles over the angular range of the x-ray system 10. Specifically, during tomosynthesis, similar to mammography, the breast is compressed between the compression paddle 40 and the detector 18. The radiation source 16 is then rotated from −θ to +θ, and a plurality of projection images of the compressed breast is obtained at regular angular intervals over the angular range. For example, if the angular range of the x-ray system is ±11 degrees, 22 projection images may be captured by the detector during an angular sweep of the gantry at approximately one every one degree. The plurality of projection images are then processed by the controller 44 to generate a plurality of DBT image slices. The processing may include applying one or more reconstruction algorithms to reconstruct three dimensional image of the breast.

Furthermore, the x-ray system may be configured to perform a DBT-guided biopsy procedure. Accordingly, in some exemplary embodiments, the system 10 may further include a biopsy device (not shown) comprising a biopsy needle for extracting a tissue sample for further analysis.

In one exemplary embodiment, the biopsy device may include a biopsy table (not shown) that is positioned over the detector 18 of the x-ray system 10. For example, the biopsy table may be configured to slide over the detector 18. During set-up of the biopsy device, the user may remove the compression paddle 40 of the x-ray system 10, and slide the biopsy table over the detector 18. Upon positioning the biopsy device 140 on the x-ray system 10, a suitable compression paddle for biopsy (not shown), such as a horizontal paddle or vertical paddle, depending on the type of biopsy, may be selected and coupled to the x-ray system 10.

The biopsy device may further include a biopsy tool interface having a biopsy tool display. The biopsy tool interface may be coupled to the biopsy table via a communication port. In one embodiment, the biopsy tool interface may be communicatively coupled with the x-ray system controller 44, and as such, the user may be able to adjust a position of the x-ray system, such as adjusting the gantry to a park position, via the biopsy tool interface. In other embodiments, the biopsy tool interface may be coupled to a biopsy device controller, which sends and receives information to and from the x-ray system controller 44. In some other embodiments, additionally or alternatively, adjustment and control of the biopsy device 1 may be performed by a biopsy device control module of the x-ray system controller 44.

The biopsy device may include a biopsy tool that may be directly coupled to the biopsy table. The biopsy tool may include a biopsy gun holder for mounting a biopsy gun. Further, the biopsy gun holder may include a mechanical stop for adjusting a position of a biopsy needle. The biopsy needle may include an outer cannula, an inner cannula positioned therein, and an opening for receiving a portion of tissue from the biopsied lesion or target. The cannulas form a cutting device wherein the outer cannula is configured to slide or rotate over the inner cannula, and/or the inner cannula is configured to slide or rotate within the outer cannula.

During biopsy, prior to inserting the needle, the breast is positioned between a compression paddle (not shown) and a top surface of the table. In some examples, a breast spacer may be positioned on the surface, and the breast is positioned between the compression paddle and the spacer, and compressed by moving the compression paddle toward the surface. Upon positioning the breast, a first set of targeting images are obtained by the scanning the compressed breast with x-ray system 10 at various angles over its angular range to identify a target for biopsy. The first set of targeting images may be three dimensional images (DBT images) or two-dimensional full field digital mammography images reconstructed from the x-ray system acquisitions. The user may localize the concerned region and identify a target position for biopsy by selecting the target position from the first set of images. The target position may be identified by x, y, and z coordinates within a DBT volume between the compression paddle and the biopsy table surface or spacer (if used). Based on the target position coordinates selected by the user, the biopsy device controller may adjust the mechanical stop position of the biopsy gun holder such that when the needle is inserted into the compressed breast via the biopsy gun, the needle movement is stopped when the needle tip reaches a desired position (referred to as pre-fire position) with respect to the target position. While the present example illustrates adjustment of the biopsy device via the biopsy device controller, it will be appreciated that in some embodiments, the x-ray system controller 44 may command control of the biopsy device.

Once the biopsy tool and the biopsy gun are at target position, the user/radiologist may drive the needle through the biopsy gun until it reaches the mechanical stop. Once fully inserted, the needle is then at the pre-fire position (that is, the position where a notch of the needle is in front of the lesion to puncture). Subsequently, a second set of images with the biopsy needle at the pre-fire position is obtained. The user may then initiate firing of the biopsy needle via the biopsy gun. Once the biopsy needle is fired, at least one biopsy sample may be removed from the body part, such as a patient's breast, by use of aspiration and/or the cutting mechanism formed by the inner and outer cannulas. The sample is moved by aspiration down an aspiration tube coupled to a collection chamber with individual pre-labeled chambers to delineate the order or location of each sample from the biopsy procedure. Alternative means of labeling each sample allowing for location identification and/or order identification may also be employed. Further, after needle firing, a third set of images with the needle in the post-fire position may be obtained.

The mammography system 100 may further include one or more vision sensors for sensing one or more components and accessories of the mammography system 100. The one or more vision sensors may include a first camera 101 and a second camera 102, as shown in FIG. 1A. The first camera 101 may be configured to sense one or more components and accessories associated with the x-ray system 10, while camera 102 may be configured to sense one or more of user interfaces, including the display 50 and a display portions visible on the display 50, of the workstation 43. Further, any of the cameras 101 and 102 may be configured to sense one or more user and patient actions. While the present example, illustrates two cameras for sensing each of the x-ray system 10 and the workstation, it will be appreciated that the vision system may include fewer or additional cameras.

In one exemplary embodiment, more than two cameras may be used. For example, while one camera may be used to monitor the x-ray system 10, and another camera may be used to monitor the workstation, one or more additional cameras may be used to monitor one or more accessories, such as the biopsy device. Further, the one or more additional cameras may be configured to monitor specific motions, such as firing of the biopsy needle. Furthermore, any of the cameras may be configured to detect one or more of user presence, patient presence, user position, patient position, user movement, and patient movement.

An exemplary embodiment of a vision system including one or more cameras for monitoring one or more accessories is shown at FIG. 1B. Specifically, a first camera 151, a second camera 152, a third camera 153, and a fourth camera 154 coupled to a portion of an X-ray system 150 are illustrated. X-ray system 150 is similar to X-ray system 10 discussed at FIG. 1A, and hence the description of similar components and elements will not be repeated here for the sake of brevity. Briefly, X-ray system 150 includes a gantry 158 comprising a radiation source 160, a radiation detector 168, and a collimator (not shown) coupled to a support structure 170. The X-ray system 150 further includes a compression paddle 164 for holding a body part, such as a breast, in place against a top surface of the radiation detector 168. The compression paddle 164 may be coupled to a support rail 172 of the gantry 158, and is movable upward and downward along the support rail in a direction away and toward the radiation detector 168. The movement of the gantry 158 and the compression paddle 164 may be controlled via respective actuators based on signals from a controller (not shown), such as a controller 44 at FIG. 1A, communicatively coupled to the X-ray system 150. The gantry 158 may rotate clockwise and anticlockwise to a desired degree about a vertical axis of the support structure.

The first camera 151 and the second camera 152 may be positioned adjacent to key pad controls 181 and 182 on the gantry 158. The first camera 151 and the second camera 152 are positioned on opposite sides of the gantry and may be used to monitor right side view and left side view of the patient during a procedure, such as mammography imaging or biopsy, performed by the X-ray system 150. In one example, each of the first and second cameras 151 and 152 may be configured as video cameras. Other embodiments where the first and second cameras 151 and 152 are configured as other types of cameras, such as wide angle camera, are also within the scope of the disclosure. Further, other embodiments where the first and second cameras 151 and 152 are configured as other types of cameras such as RGB-D cameras that combine depth information with RGB color information or depth cameras are also within the scope of the disclosure Image sequences captured by the first and the second camera may be stored in a memory of the controller.

The third camera 153 may be positioned on the gantry 158 above a top position of the compression paddle 164. Thus, the third camera 153 may be fixed with respect to the gantry 158. The fourth camera 154 may be positioned on the compression paddle 164 and thus, is movable with respect to the gantry 158. In one example, the third camera 153 and the fourth camera 154 may be each configured as a fish-eye type of wide angle camera. It will be appreciated that other types of camera, such as video camera, other type of wide-angle camera, or RGB-D cameras are also within the scope of the disclosure. In one example, the third camera 153 may be utilized as an accessory monitoring camera for detecting the presence and position of one or more accessories associated and/or used with the X-ray system 150. The one or more accessories may include mammography imaging associated accessories, such as quality check associated accessories, such as QC phantoms, and biopsy related accessories, such as biopsy device, biopsy needle, biopsy spacer, and anesthesia needle. The fourth camera 154 may also be used for accessory monitoring, particularly during mammography and biopsy procedures. Due to the positioning of the fourth camera on the compression paddle, the fourth camera 154 may be used to obtain closer view of biopsy related accessories. Further, in addition to monitoring the accessories, the images from the third and the fourth cameras 153 and 154 may also be used to monitor one or more patient parameters.

Further, one or more of the first camera 151, the second camera 152, the third camera 153, and the fourth camera 154 may be used for monitoring a biopsy needle firing event during the biopsy procedure.

In one exemplary embodiment, depending on the occlusions generated by the biopsy device and/or user, one camera or a combination of cameras could be used for detecting the needle firing event. For example, a camera that provides most information depending on the occlusions may be selected, and used for detecting the needle firing event.

In another exemplary embodiment, as the biopsy needle firing has a sound profile, the biopsy needle firing event may be detected based on the sound profile produced by the firing event. For example, a sound sensor, such as a sound recorder and analyzer, may be coupled to the x-ray system or positioned within an examination room where the procedure is performed. The sound recorder and analyzer may detect the biopsy needle firing event based on one or more of frequency, amplitude, and duration of the sound produced during the biopsy needle firing event.

In yet another exemplary embodiment, a combination of sound and vision sensing may be used to detect the biopsy needle firing event.

Further, the image sequences captured by the first, second, third, and fourth cameras 151, 152, 153, and 154 may be pre-processed to extract relevant image data and the processed image data may be used as input into a deep learning model comprising a neural network such as a convoluted neural network for providing a comprehensive workflow monitoring.

Figure 9:
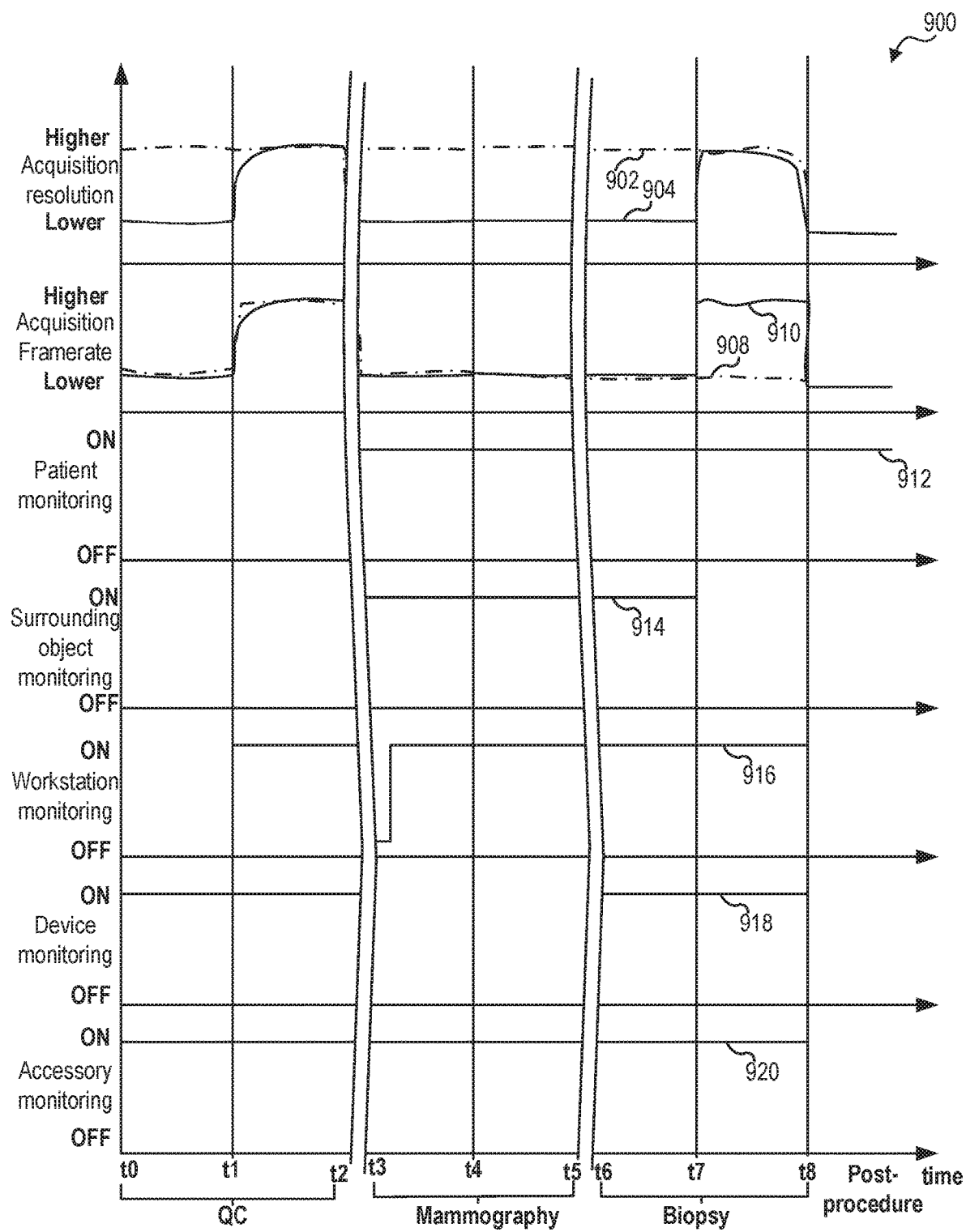
FIG. 9 shows an exemplary workflow monitoring during example quality check, mammography, and biopsy procedures, according to an embodiment of the disclosure.

An example workflow sequence monitoring of an X-ray system utilizing the vision system including the first, second, third, and fourth cameras is illustrated at FIG. 9. Further, the vision system discussed herein with respect to FIG. 1B may be used in conjunction with one or more of the vision sensors 101 and 102 at FIG. 1A.

Figure 3:
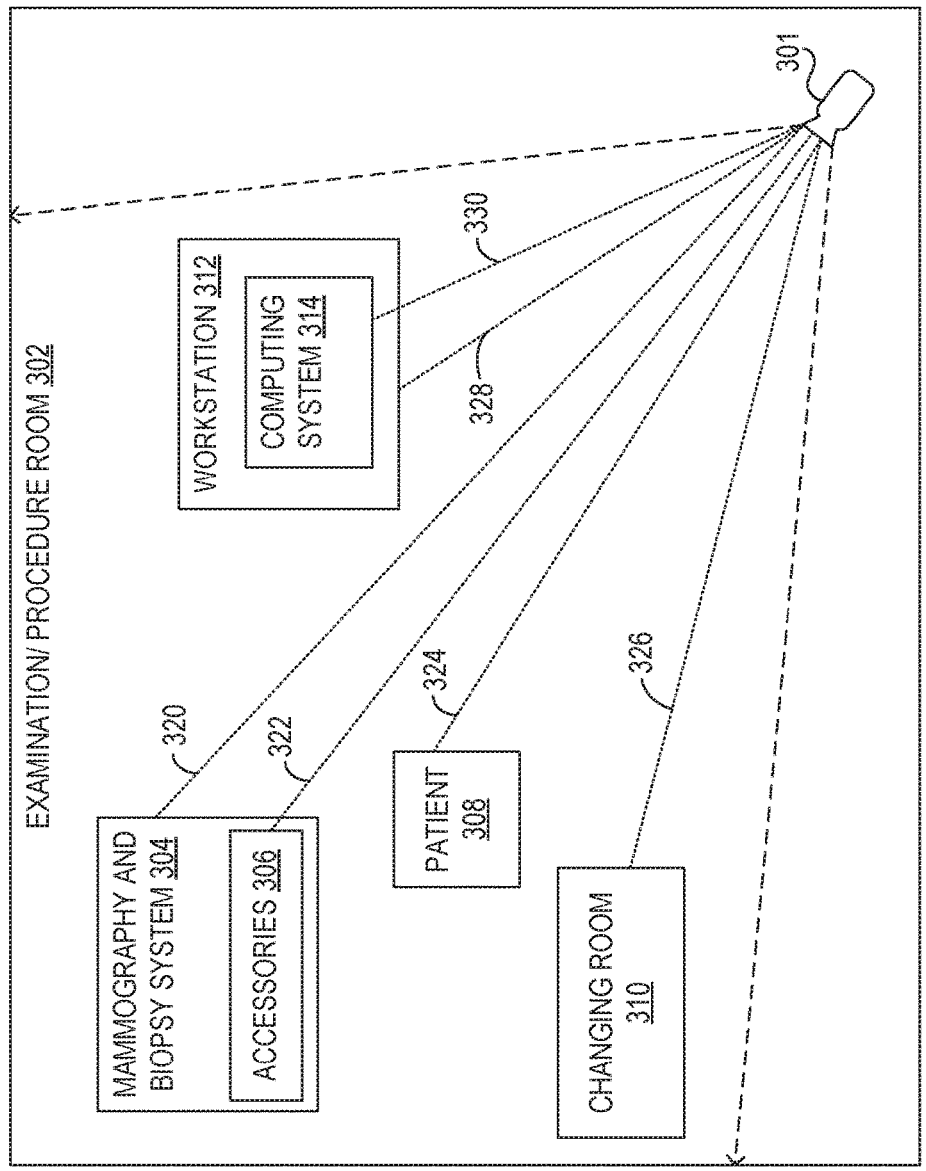
FIG. 3 is a block diagram illustration of a top view of an examination room including a mammography system and a vision sensing system, according to an embodiment of the disclosure.

While the above embodiments illustrate using two or more cameras for the vision system for workflow monitoring of the X-ray system, in another exemplary embodiment, as shown in FIG. 3 below, a single camera may be used to sense and monitor the x-ray system, the workstation, and an entire examination/procedure room including the user, and the patient in addition to the above mentioned systems and components.

In yet another exemplary embodiment, a camera (not shown) may be positioned on the gantry such that a field of view of the camera encompasses the compression paddle 164 and the imaging volume between the compression paddle 164 and the detector 168. One or more images from the camera may be used to detect the rims of the camera, and detect one or more of contours, openings, recesses, bends, and textures on the portion of the compression paddle between the rims of the compression paddle. Based on the detected attributes of the compression paddle, the vision system may determine a type of compression paddle used with the mammography system.

Returning to FIG. 1A, the one or more vision sensors may be communicatively coupled to the controller 44. Details of the various components of the mammography system 100 that may be sensed and monitored by the one or more cameras 101 and 102, and the various actuators of the mammography system 100 that may be adjusted in response to the sensing and monitoring by the cameras will be further elaborated with respect to FIG. 2 below.

Turning to FIG. 2, a block diagram of a mammography system 200 is shown. The mammography system 200 may be a non-limiting example of the mammography system 100 at FIG. 1. Briefly, the mammography system 200 may be utilized to perform one or more of a mammography procedure, such as a digital breast tomosynthesis, and a biopsy procedure, such as a stereotactic biopsy or x-ray guided biopsy. The mammography system 200 may include a medical vision system 250 having at least a vision sensor system 252 and a processing system 256 to perform one or more of sensing, monitoring, and analyzing of one or more accessories and components associated with the mammography system 200. Further, the mammography system 200 may be automatically adjusted, controlled, and set-up via the processing system 256 based on the input from the vision sensor system 252 and the analysis of the input by the processing system 256, to improve workflow during one or more of the mammography and biopsy procedures performed with the mammography system 200. The processing system 256 may be an non-limiting example of controller 44 at FIG. 1, and may be configured to receive signals form one or more sensor systems of the mammography system 200, including the vision sensor system 252, as further discussed below. The processor may be further configured to analyze the data received from the sensor systems, and adjust operation of the mammography system 200 via one or more x-ray system actuators 276, in addition to providing one or more alerts and indications to one or more of the user and the patient via a user interface 286 of the mammography system 200 as further discussed below.

The mammography system 200 may include an x-ray system 210, and a medical vision system 250. X-ray system 210 may be an example of X-ray system 10 discussed at FIG. 1A, or x-ray system 150 at FIG. 1B. In one exemplary embodiment, the x-ray system 210 may be configured as a medical imaging modality for performing a mammography procedure to image and analyze a body part of a patient, such as a breast. In another exemplary embodiment, the x-ray system 210 may be configured for performing a biopsy procedure, such as an x-ray guided biopsy to obtain a tissue sample from the body part of the patient. Further, the x-ray system 210 may be converted from a mammography system for obtaining medical scan images to a biopsy system to perform a biopsy procedure for extracting tissue for evaluation. When the x-ray system 210 is utilized to perform a biopsy procedure, a biopsy device 212 may be coupled to the x-ray system 210. The biopsy device 212 may be an example of the biopsy device described at FIG. 1A, and may include a biopsy table, a biopsy tool, a biopsy tool interface, a biopsy gun holder, and a biopsy gun. Further, the biopsy device 212 may include one or more biopsy device accessories 214 coupled to one or more of the x-ray system 210 and the biopsy device 212. The one or more biopsy device accessories 214 may include a needle 216 for entering the body part and extracting a tissue portion for further analysis by a clinician, an adaptor 218, a biopsy spacer 220 for use as a support for the body part and to obtain desired positioning of the body part with respect to the needle 216 during biopsy, a compression paddle 222 for supporting the body part and holding the body part so as to reduce movement during biopsy, and one or more phantom 224 for performing quality check prior to mammography or biopsy. The compression paddle 222 is an example of compression paddle 40 described with respect to FIG. 1A or compression paddle 164 at FIG. 1B. The mammography system may be configured to monitor, via the medical vision system 250, one or more of components, such as the biopsy device 212, different components of the biopsy device 212, and accessories, such as biopsy device accessories 214.

In one exemplary embodiment, the vision system 250 may be utilized to detect the presence of the compression paddle 222. Further, upon detecting the compression paddle, the vision system 250 may generate one or more images of the compression paddle 222. The one or more images of the compression paddle 222 may then be utilized to identify a type/classification of the compression paddle based on one or more attributes of the compression paddle 222.

The one or more attributes of the compression paddle 222 may include a distance between a left rim and a right rim of the paddle, presence or absence of one or more openings/ recess on a top surface of the paddle between the left and the right rim, presence or absence of textural difference in the middle of the paddle, presence or absence of one or more bends on the surface of the paddle between the left and the right rims, and shape of the paddle. Based on the detected attributes, the vision system 250 may identify the type of compression paddle attached to the system. For example, the side rims of the compression paddle may be identified, and a distance between the rims may be calculated. Further, based on the one or more images of the compression paddle, the vision system may determine if one or more other attributes of the compression paddle surface between the rims, such as contours, openings, recesses, bends, and/or textures may be detected. The rim distance and the other attributes of the compression paddle may be utilized to identify the type of compression paddle currently used with the mammography system. In some examples, based on the type of compression paddle identified, the vision system 250 may determine a mode of operation. As an example if a compression paddle specific for biopsy is detected (e.g., biopsy paddle), the vision system may determine that the user intends to operate the mammography system in the biopsy mode.

Further, additionally or alternatively, a change in position of the compression paddle 222 may be monitored with the vision system 250. As an example, during a mammography exam or a biopsy exam, in order to adjust breast position, the user may move the compression. The vision system 250 may detect a movement of the compression paddle 222, and based on the changed position of the compression paddle, the controller may command adjustment of a collimator such that the breast is within the field of view of the x-ray system.

Furthermore, in some embodiments, the vision system may be utilized to determine a final (locked) position of the compression paddle in addition or alternative to user confirmation of compression paddle position via the user interface. The final compression paddle position may indicate that the breast is in position for imaging. Upon confirming the final position of the compression paddle, the mammography system may automatically begin acquisition of images of the compressed breast.

The mammography system 200 may be further configured to monitor an environment 226 surrounding the x-ray system 210 using the medical vision system 250. The environment 226 may include one or more of a workstation 228, a specimen 230, such as a body part, for imaging, a wheelchair 232 depending on the patient needs, a biopsy bed 234 depending on the type of biopsy performed and the patient physiology, a patient 236, and a user 237. Furthermore, the mammography system 200 may be configured to monitor, via the medical vision system 250, one or more of a process, a movement, and an action with respect to the x-ray system 210 and the environment 226.

As indicated above, the medical vision system 250 includes a vision sensor system 252 comprising one or more cameras 254, and an image processing system 256 comprising a processor 258, and a non-transitory memory 260. The vision sensor system 252 may be communicatively coupled to the image processing system 256. Specifically, the processing system 256 may receive one or more signals from the one or more cameras 254 of the vision system. The one or more cameras of the vision system 252 may be similar to cameras 101 and 102 discussed with respect FIG. 1A, and as such, the one or more cameras 254 may sense the mammography system 200 and its components, accessories, and environment. Data from the one or more cameras 254 may be sent to the processing system 256 for further analysis and storage.

In one exemplary embodiment, the vision sensor system 252 including one or more cameras 254 may include two vision sensors (two cameras) as shown in FIG. 1A. In another exemplary embodiment, the vision sensor system 252 may include a set of cameras, including the first camera 151, the second camera 152, the third camera 153, and the fourth camera 154 coupled to the x-ray system 150 discussed with respect to FIG. 1B. In yet another embodiment, the vision sensor system may include a single stand-alone camera, as shown in FIG. 3. Additionally, the vision sensor system 252 may include any combination of the above embodiments.

The processing system 256 includes a processor 258 configured to execute machine readable instructions stored in the non-transitory memory 260. Processor 258 may be single core or multi-core, and the programs executed thereon may be configured for parallel or distributed processing. In some embodiments, the processor 258 may optionally include individual components that are distributed throughout two or more devices, which may be remotely located and/or configured for coordinated processing. In some embodiments, one or more aspects of the processor 258 may be virtualized and executed by remotely-accessible networked computing devices configured in a cloud computing configuration. According to other embodiments, the processor 258 may include other electronic components capable of carrying out processing functions, such as a digital signal processor, a field-programmable gate array (FPGA), or a graphic board. According to other embodiments, the processor 258 may include multiple electronic components capable of carrying out processing functions. For example, the processor 258 may include two or more electronic components selected from a list of electronic components including: a central processor, a digital signal processor, a field-programmable gate array, and a graphic board. In still further embodiments the processor 258 may be configured as a graphical processing unit (GPU) including parallel computing architecture and parallel processing capabilities.

Non-transitory memory 260 may store a neural network module 262, camera image data 264, accessory monitoring module 266, user input monitoring module 268, environment monitoring module 270, workflow monitoring module 272, and patient monitoring module 274. Neural network module 262 may include a deep learning module, comprising a plurality of parameters (including weights, biases, activation functions), and instructions for implementing the one or more deep neural networks to receive image data from the vision sensor system 252, and identify one or more of objects corresponding to one or more of the x-ray system components and accessories, and further identify one or more environmental parameters, and further still, identify one or more processes and actions related to one or more of mammography and biopsy. For example, neural network module 262 may store instructions for implementing a deep learning module comprising one or more neural networks, such as a convolutional neural network (CNN). Neural network module 262 may include trained and/or untrained neural networks and may further include various data, or metadata pertaining to the one or more neural networks stored therein. Non-transitory memory 260 may further store a training module (not shown), which comprises instructions for training one or more of the deep neural networks stored in neural network module 262.

Furthermore, using input from the vision sensor system 252, the deep learning module may identify a current work flow step, including a quality check procedure, a mammography imaging procedure, and a biopsy procedure, and set-up the mammography system based on the identified workflow step. Further, using input from the vision sensor system 252, the deep learning module may determine errors in the procedure by evaluating if one or more actual procedure parameters match one or more user input variables as entered by the user into the user interface (e.g., compare actual biopsy device type with biopsy type selected in the workstation user interface, compare actual needle size with needle size entered in the user interface, compare presence of spacer with indication of spacer presence or absence in the user interface, etc.), and control the mammography system and provide alerts based on the errors detected. Details of identifying the current work flow step, determining errors during the procedure and adjusting the mammography system based on the detected workflow step and errors will be further elaborated below with respect to the methods described at FIGS. 4A, 4B, 5A, 5B, 6A and 6B.

Non transitory memory 260 may further store camera image data 264. Camera image data 264 may include images captured by the vision sensor system 252. For example, images captured by the vision sensor may include images of the one or more mammography system, including x-ray system 210 including its components and accessories, the environment 226, and processes and/or actions associated with the x-ray system 210 and the environment 226. Camera image data 264 may further include patient monitoring images.

Non-transitory memory 260 may further store the accessory monitoring module 266 including instructions for monitoring and analyzing the presence and current positions of the one or more accessories 214 and biopsy device 212.

Non-transitory memory 260 may further store the user input monitoring module 268 including instructions for monitoring and analyzing user input via a user interface (such as a display screen or display screen portion).

Non-transitory memory 260 may further store the environment monitoring module 270 including instructions for monitoring and analyzing the environment 226, and may store workflow monitoring module 272 including instructions for monitoring and analyzing one or more process and action 238. Further still, non-transitory memory 260 may store patient monitoring module 274 for monitoring and analyzing one or more of patient presence, patient position, and patient movement into and out of the examination room. Additionally, non-transitory memory 260 may store a user monitoring module for monitoring and analyzing one or more of user presence, user position, and user movement into and out of the examination room.

Non-transitory memory 260 may further store medical image data 275. The medical image data 275 may include scan images of the body part captured by the x-ray system 210.

Upon sensing and analyzing one or more of the x-ray system 210, the environment 226, and process and action 238, the image processing system 256 may output instructions to one or more x-ray system actuators 276 based on the sensing and the analyzing. The x-ray system actuators 276 may include image acquisition actuator 278 for controlling a radiation source output from a radiation source such as radiation source 16 at FIG. 1, gantry motion actuators 280 for controlling gantry position of the x-ray system 210, and a bed position actuator for adjusting a biopsy bed position, for example, based on presence or absence of an object in the environment 226 such as the wheel chair 232. The gantry motion actuator(s) 280 may include one or more actuators for adjusting one or more of a gantry lift, a gantry rotation, and a gantry angulation, where the gantry lift motion includes movement of the gantry in an upward or downward direction along the vertical axis of the x-ray system 210, the gantry rotation is the rotation of the detector and the x-ray generation tube around a rotation axis, and the gantry angulation is the rotation of the x-ray tube while the detector remains still within an angular range of rotation.

The x-ray system actuators 276 may further include a biopsy device actuator for adjusting operation of the biopsy device, such as firing of the biopsy needle, for example, based on sensing one or more inconsistencies between the user input and the actual x-ray system configuration as further detailed below. The x-ray system actuators 276 may further include a compression paddle actuator 285 for adjusting movement of the compression paddle 222.

Further, upon sensing and analyzing one or more of the x-ray system 210, the environment 226, and process and action 238, the image processing system 256 may output one or more alerts via a user interface 286. The user interface 286 may be an example of user interface 56 at FIG. 1A. The one or more alters output by the processing system 256 via the user interface 286 may include one or more of a visual alert 288 and an audible alert 290. Other types of alerts, such as haptic alerts, are also within the scope of the disclosure. Further, the processing system 256 may be configured to update image acquisition input 292 on the user interface 286 and adjust one or more of x-ray system set-up, configuration, and operation accordingly. Further still, the processing system may be configured to update accessory information input 294 on the user interface 286 and adjust x-ray system set-up, configuration, and operation accordingly.

Details of adjusting the various actuators based on the various inputs, and the details of the various alerts and updates to the user interface of the x-ray system will be described with respect to FIGS. 4A-4B, 5A-5B, 6A-6B, 7, 8, and 9 respectively.

It should be understood that image processing system 256 shown in FIG. 2 is for illustration, not for limitation. Another appropriate image processing system may include more, fewer, or different components.

Turning to FIG. 3, a top view of an examination room 302 is schematically illustrated. The examination room 302 includes a camera 301 to monitor an x-ray system 304, where the x-ray system 304 is an example of the x-ray system 10 at FIG. 1 and x-ray system 210 at FIG. 2. In this example, the camera 301 is configured as a stand-alone camera. Thus, as indicated by 320 and 322, camera 301 receives image information from the x-ray system 304 including image information regarding one or more accessories 306 associated with the x-ray system 304. The accessories 306 may be an example of accessories 214 at FIG. 2 and may include one or more objects in the environment 226 at FIG. 2 such as specimen 230. Further, camera 301 may be utilized to monitor one or more of a patient 308 (as indicated by 324), a changing room 310 (as indicated by 326), a work station 312 (as indicated by 328) and a computing system 314 (as indicated by 330). The camera field of view may encompass the entire examination room 302, as depicted by the broken line with end arrows. While the example at FIG. 3 shows camera positioned at a top corner of the room 302, other suitable positions where the camera can capture the various devices and objects in the examination room are also within the scope of the disclosure. Further, embodiments where more than one camera is utilized for monitoring the entire room are also within the scope of the disclosure.

Next, FIG. 4 shows a high-level flow chart illustrating an example method 400 for detecting an exam configuration based on vision sensing of one or more of accessories associated with an x-ray imaging system, such as x-ray system 10 at FIG. 1 or x-ray system 210 at FIG. 2, and an environment surrounding the x-ray imaging system, such as environment 226 at FIG. 2, and adjusting an x-ray system configuration based on the detected exam configuration. Method 400 may be implemented by an image processing system, such as processing system 256 at FIG. 2, or controller 44 at FIG. 1, an edge device connected to the image processing system, a cloud in communication with the image processing system, or any appropriate combination thereof. Method 400 is described with regard to the systems and components of FIGS. 1A, 1B, 2, and 3, although it should be appreciated that method 400 may be implemented with other systems and components without departing from the scope of the present disclosure.

Method 400 begins at 402. At 402, method 400 includes monitoring one or more of user and patient in an examination room, such as examination room 302 at FIG. 3. In an exemplary embodiment, the monitoring of the one or more of the user and the patient may be based on facial recognition of the one or more of the user and the patient via a neural network protocol implemented by the processor.

Next, at 402, method 400 includes confirming if one or more of the patient and the user are present in the room. If yes, method proceeds to 406. Otherwise, method 400 may continue to monitor for the presence of one or more of the user and the patient.

At 406, method 400 includes receiving images from one or more cameras, such as cameras 101 and 102 at FIG. 1A, the first, second, third, and fourth cameras 151, 152, 153, and 154 at FIG. 1B, cameras 254 at FIG. 2, or camera 301 at FIG. 3. The images from the one or more cameras may include images of the x-ray system, the x-ray system components, and the x-ray system accessories.

Next, method proceeds to 408 to determine exam configuration based on vision sensing from the one or more cameras. Determining exam configuration may include at 408, identifying one or more biopsy accessories currently associated with the system. The one or more biopsy accessories may include a biopsy device, such as biopsy device 211 at FIG. 2, a biopsy needle, such as biopsy needle 216 at FIG. 2, a biopsy adaptor such as biopsy adaptor 218 at FIG. 2, a biopsy spacer, such as biopsy spacer 220 at FIG. 2, a compression paddle, such as paddle 222 at FIG. 2, and one or more phantom, such as phantom 224 at FIG. 2. Further, determining exam configuration may include at 410, determining presence of specimen, such as a body part (e.g., breast for x-ray systems), a quality check (QC phantom) in the field of view of a radiation source, such as radiation source 16 at FIG. 1A in the volume between the top surface of the radiation detector and the radiation source or compression paddle, if compression paddle is attached to the system. Further, determining exam configuration may include at 412, determining presence of one or more surrounding objects in an environment of the x-ray system, including a wheel chair, such as wheel chair 232 at FIG. 2, and a biopsy bed, such as biopsy bed 234 at FIG. 2. Further, determining exam configuration may include at 414, determining one or more parameters of each of the one or more accessories, specimen, and surrounding objects identified with the x-ray system. The one or more parameters may include confirmed presence of the one or more accessories, specimen, and surrounding objects, and position of the one or more accessories, specimen, and surrounding objects with respect to the x-ray system and the patient.

Next, method 400 proceeds to 416 (continued at FIG. 4B). At 416, method 400 includes determining if the accessories, specimen and surrounding objects indicate a desired mode of operation including a biopsy mode, a mammography mode, and a quality check mode.

The desired mode of operation of the x-ray system may be a quality check mode if a quality check phantom is detected in the field of view. For example, the user may place the quality check phantom in the field of view. Upon detecting the presence of the QC phantom in the field of view, with the vision sensors, the processor may determine that the user intends to operate the mammography system in the quality check mode. In some examples, the QC phantom may be a flat field phantom that is used for evaluating image quality biopsy needle trajectory. In general, presence of the QC phantom on the mammography device without the biopsy device may indicate that the user intends to evaluate image quality. As such, upon detecting the presence of the QC phantom without the biopsy device, the processor may determine that the user intends to perform a quality check procedure for image quality evaluation. In other case, the user may couple a biopsy device with the x-ray gantry and place a localization phantom that is used for evaluating biopsy needle trajectory in the field of view. Upon detecting the biopsy device and the localization phantom, the processor may determine that the user intends to perform a second type of quality check for evaluating biopsy needle trajectory with the biopsy device. Additionally, in some examples, the QC mode may be confirmed based on the absence of the compression paddle.

The desired mode of operation may be a biopsy mode if a biopsy device and one or more of the biopsy device accessories are detected in the field of view of the radiation source of the x-ray system. For example, presence of the biopsy device and one or more biopsy accessories, such as biopsy paddle, biopsy spacer, biopsy needle, and biopsy adaptor connected to the x-ray system indicates that the intended use for the x-ray system is to perform a biopsy. Thus, the processor, based on the identification of one or more of the biopsy device and the biopsy device accessories, and absence of QC phantom, may determine that the x-ray system is intended to be operated in the biopsy mode.

If the biopsy device and/or the accessories are not detected associated with the x-ray system, and if one or more QC accessories are not detected associated with the x-ray system, the processor may determine that the x-ray system is intended for use in the mammography mode where the x-ray system is used only for imaging the body part, and not performing biopsy or performing the quality check.

Accordingly, if biopsy mode is confirmed, method 400 proceeds to 422 to set up the system in a biopsy mode. Setting up the x-ray system in the biopsy mode may include, at 424, automatically selecting the biopsy mode on the workstation interface. Further, automatically setting up the x-ray system in the biopsy mode may include, at 425, launching a biopsy exam interface on the user interface in response to the user selecting a launch exam button on the user interface and the vision system detecting one or more of the biopsy device and one or more biopsy accessories. Furthermore, automatically setting up the x-ray system in the biopsy mode may include, at 426, automatically changing a state of buttons with regard to the biopsy accessories in the biopsy exam interface on the workstation user interface; at 428, updating selection of biopsy device type used from a stored list on the workstation user interface, and further changing one or more other parameters based on the type of biopsy device (e.g., needle length); and at 430 updating a system speed profile (e.g., reduced system speed in response to detecting wheel chair, reduced biopsy device speed in response to detect biopsy needle mounted).

If the mammography mode is confirmed, method 400 proceeds to 418 to set up the system in a mammography mode. Setting up the x-ray system in the mammography mode may include adjusting system based on the detected accessories, specimen, and surrounding objects. Specifically, setting up the x-ray system in the mammography mode may include, at 419, launching a regular mammography exam interface on the user interface in response to the user selecting the launch exam button on the user interface. Setting up the x-ray system in the mammography mode may further include, at 420, adjusting the gantry to initial position based on the presence or absence of wheel chair, and at 421 updating the system speed profile based on the presence or absence of wheel chair. For example, if wheel chair is present, a speed of movement of gantry may be reduced. Further, a speed of movement of compression paddle may be reduced if wheel chair is detected. Thus, overall system speed may be reduced upon detecting the presence of wheel chair in the environment.

If quality check mode is confirmed, method 400 proceeds to 417 to automatically set up the x-ray system in a quality check mode based on the type of phantom detected and the other accessories detected. Setting up the x-ray system in the QC mode may include, at 423, launching a QC interface on the user interface in response to the user selecting the launch exam button on the user interface, at 419, adjusting the gantry position based on the type of QC performed, and may further include, at 423, adjusting scan parameters to QC scan parameters.

In one exemplary embodiment, an average acquisition resolution of the vision system may be adjusted during each of the biopsy, mammography, and QC set up modes. For example, for each of the biopsy, mammography, and QC set up modes, prior to set up and during set up, an average acquisition resolution of the vision system may be higher. Further, for each of the biopsy, mammography, and QC set up modes, prior to set up and during set up, an average acquisition frame rate may be lower as action detection is not required prior to or during set up in each of the biopsy, mammography, and QC modes. As such, object detection is prioritized which enables the vision system to more accurately monitor the overall x-ray system including accessories and the environment.

Upon setting up the x-ray system in the biopsy mode or mammography mode or QC mode, method 400 may return to monitoring the mammography system via the vision sensors.

In this way, based on vision sensing, including accessory sensing of one or more of presence of one or more accessories or lack thereof, environment sensing, and position sensing of the one or more accessories, with one or more cameras coupled to the x-ray system, the user intent regarding the desired mode of operation of the x-ray system may be determined, and the x-ray system may be automatically adjusted to enable the user to operate the x-system in the desired mode. As a result, accuracy and efficiency of system set-up is improved.

Next, FIG. 5 shows a flow chart illustrating an example method 500 for detecting user error, particularly user input error at a user interface, such as user interface 56 at FIG. 1, based on vision sensing of one or more of accessories associated with an x-ray imaging system, such as x-ray system 10 at FIG. 1A, x-ray system 150 at FIG. 1B or x-ray system 210 at FIG. 2, and monitoring user input via a user interface of a workstation, such as workstation 44 at FIG. 1 or workstation 228 at FIG. 2. Further, based on detecting the user error, the method 500 may include instructions to automatically control the x-ray system. Method 500 may be implemented by an image processing system, such as processing system 256 at FIG. 2, or controller 44 at FIG. 1, an edge device connected to the image processing system, a cloud in communication with the image processing system, or any appropriate combination thereof. Method 500 is described with regard to the systems and components of FIGS. 1A, 1B, 2, and 3, although it should be appreciated that method 500 may be implemented with other systems and components without departing from the scope of the present disclosure. In an exemplary embodiment, method 500 may be performed after detecting the system configuration via the vision system and automatically setting up the x-ray system as discussed above with respect to FIG. 4. Specifically, error detection discussed with respect to FIG. 5 may be performed when operating the x-ray system in any of the biopsy, mammography, and quality check modes after the x-ray system is automatically set up as discussed above. Steps 502, 504, and 506 are similar to steps 402, 404, and 406 at FIG. 4, and will not repeated for brevity.

Turning to 508, method 500 includes determining current system state based on vision sensing of one or more accessories from one or more cameras. Determining current system state includes determining a workflow step during a current procedure (e.g., biopsy, mammography, or QC) performed with the x-ray system. Thus, determining current system state includes, at 510, identifying presence of one or more accessories currently present in the system based on vision sensing including needle length, biopsy adaptor, breast spacer (including biopsy spacer), biopsy device, compression paddle, and QC phantom. Determining current system state further includes, at 511, determining one or more parameters of the one or more accessories identified including needle length, biopsy adaptor position, location of breast spacer, type of biopsy device, paddle parameters, phantom orientation, and phantom type.

Upon determining the current system state and the parameters of the one or more accessories in the current system state, method 500 includes, at 512, determining user action based on user input. This includes, at 514, identifying, with the x-ray system controller, one or more parameters of the identified accessories based on user input into the user interface (UI) including needle length input, biopsy adaptor position input, and indication of presence or absence of breast spacer, biopsy device type input, paddle parameters input, and phantom parameters input. Additionally, at 516, method 500 includes identifying, with the with the x-ray system controller, one or more parameters of remaining potential accessories based on user input into the user interface (UI).

While the above example illustrates determining user input by the x-ray system controller, in one exemplary embodiment, the user action at 514 and 516 discussed above may be determined based on vision sensing of workstation from one or more cameras. Example monitoring of one or more parameters based on user input into the workstation interface and vision sensing of the workstation and the user interface is shown at FIG. 7.

Briefly turning to FIG. 7, a schematic illustration 700 of monitoring a portion of a workstation 703 via a workstation camera 701, according to an exemplary embodiment, is shown. Workstation 703 may be an example of workstation 44 at FIG. 1A. The camera 701 is an example of camera 102 at FIG. 2. As indicated by dotted lines at 720, 722, and 724, the camera 701 reads one or more user inputs or user selections 706, 708, and 712 on a user interface 702 of the workstation 703. Based on reading the inputs entered into the user interface 704 by the user, the processor may determine the parameters input by the user.

Returning to FIG. 5, upon determining user action based on workstation monitoring, method 500 proceeds to 518 (continued at FIG. 5B). At 518, method 500 includes determining if there is any inconsistency between the current system state (as detected at 508 based on the one or more accessories) and the user action (as determined at 511 based on the user input monitoring) while operating the system in each of the biopsy, mammography, and QC modes.

Specifically, during biopsy procedure, the processor may determine if the biopsy device type indicated by the user on the user interface matched with the actual biopsy device type of the biopsy device coupled to the x-ray system. Further, the processor may determine if the needle length input by the user matches the needle length on the biopsy device coupled to the x-ray system. Furthermore, during biopsy procedure, the processor may determine if the indications regarding the accessories, such as presence of biopsy spacer, matches with the actual configuration of the x-ray system. Further, the processor may determine if the type of approach selected by the user on the user interface (horizontal versus vertical) matches the configuration of the biopsy device coupled with the x-ray system.

During mammography procedure, the processor may determine if the indications by the user on the user interface regarding the accessories, such as presence of spacer, matches with the actual configuration of the x-ray system.

During quality check procedure, the processor may determine if the user selection on the user interface with respect to phantom type (e.g. localization or flat-field phantom) and parameters (e.g. orientation of the phantom with respect to a pin phantom) matches the actual phantom type and parameters currently utilized with the x-ray system.

If the user action and the actual system set-up do not match, the processor may confirm inconsistency between the current system state and user input, and may proceed to 522. At 522, the inconsistency may be identified, and subsequently, at 524, method 500 includes, automatically controlling the x-ray system. Automatically controlling the x-ray system may include, at 526, ceasing image acquisition or preventing a next step in the procedure (e.g. needle firing). Further, upon detecting inconsistency between the current system state and user input, method 500 may include, at 528, providing an alert to the user regarding the inconsistency. The alert may be one or more of an audible alert and a visual alert.

An example of an inconsistency is described below at FIG. 8 with respect to a biopsy spacer accessory of a biopsy device associated with an x-ray system, such as system 10 at FIG. 1A, system 150 at FIG. 1B, or system 200 at FIG. 2. The biopsy device may be monitored by a camera. An example monitoring of a biopsy spacer 804 is schematically illustrated with respect to FIG. 8. At FIG. 8, a camera 801, which may be an example of a camera such as camera 101 at FIG. 1A, one or more of cameras 153 and 154 at FIG. 1B, or camera 254 at FIG. 2, or camera 301 at FIG. 3, may be used to monitor a biopsy device. A portion 800 of the biopsy device is shown at FIG. 8 including a needle 808, a base support 806, and the biopsy spacer 804. A body part 802 (e.g., breast) is shown positioned on the spacer 804 of the breast spacer 804. The camera 801 senses the needle 808 as indicated at 822. Further, the camera 801 senses the presence of the breast spacer 804, as indicated at 820, and the presence of the body part 802 on the breast spacer.

Further, the x-ray system processor may monitor the user indications as input by the user and detect that the breast spacer indication button is turned off. As the breast spacer indication is turned off (due to an error by the user, that is, the user failing to indicate the presence of the breast spacer), the x-ray system may be set up such that the needle is positioned to fire based on the indication that the breast spacer is off. Hence, the needle is positioned lower than desired and aligned with the spacer instead of the breast as shown at FIG. 8. upon sensing the presence of the breast spacer based on vision sensing, and detecting that the breast spacer indication on the user interface is in error, the processor may determine an inconsistency between the user action and the actual system set up. Accordingly, an alert may be provided to the user regarding the specific inconsistency identified. Further, the processor may inhibit a next step in the procedure, such as needle firing, in order to prevent the user from injecting the spacer with the needle.

As another example, inconsistency may be determined and indicated when a wrong phantom is used (e.g., using an image quality phantom instead of a localization phantom). In yet another example, inconsistency may be detected based on a wrong needle length entered in the user interface (e.g., when a the user selects at the user interface a 15 cm needle length biopsy device configuration whereas the vision system detects that the needle length is different form the user selection).

Returning to 518, if no inconsistency is detected, method 500 proceeds to 520 to continue monitoring accessories and user input until patient and/or user leaves the room.

In this way, workflow during a procedure (e.g., biopsy, mammography, or QC) performed with the x-ray system may be monitored based on one or more of accessory monitoring with the vision system and user interface monitoring, and one or more errors during the procedure may be identified and indicated to the user.

Turning next to FIG. 6, an example method 600 for detecting specific work flow steps using the vision system and providing one or more of a voice alert, a voice guidance, an automatic system update, and a motion inhibition, is shown. Method 600 may be implemented by an image processing system, such as processing system 256 at FIG. 2, or controller 44 at FIG. 1, an edge device connected to the image processing system, a cloud in communication with the image processing system, or any appropriate combination thereof. Method 600 is described with regard to the systems and components of FIGS. 1, 2, and 3, although it should be appreciated that method 600 may be implemented with other systems and components without departing from the scope of the present disclosure. In an exemplary embodiment, method 600 may be performed after detecting the system configuration via the vision system and automatically setting up the x-ray system as discussed above with respect to FIG. 4.

Method 600 begins at 602, which includes receiving images from one or more cameras, such as cameras 101 and 102 at FIG. 1A, the first, second, third, and fourth cameras 151, 152, 153, and 154 at FIG. 1B, cameras 254 at FIG. 2, cameras 254 at FIG. 2, or camera 301 at FIG. 3. The images may include images of the x-ray system, the x-ray system components, and the x-ray system accessories.

Next, method 600 includes at 604 monitoring, with the vision sensors, one or more of accessories, user action, device movement, and patient movement. The monitoring may be performed as discussed above. Briefly, image data from the one or more vision sensors may be utilized to identify the accessories currently positioned in a field of view of the radiation source of the x-ray system, accessories coupled to the system, monitor patient position, and one or more parameters (e.g., position and orientation with respect to the x-ray system) of the accessories identified with the x-ray system.

At 606, method 600 may determine the user is performing a quality check (QC) step, for example based on detecting the presence of a QC phantom via the one or more cameras. If the answer at 606 is YES, method 600 proceeds to 608 to detect which step of the QC procedure is underway. This includes determining one or more current phantom parameters for QC based on vision sensing of the phantom and user input into the workstation UI including phantom type and phantom orientation. For example, for the QC process, upon completing the set-up, the processor may determine if the initial image acquisition has been initiated. The method then proceed to 614 to provide one or more audible messages, such as audible instructions, to assist the user in performing the QC process.

Next, method 600 proceeds to 616 to determine if QC process is complete. Completion of the QC process may be confirmed based on one or more of the user removing the phantom from the receiver surface and the user indicating via the user interface that the QC is complete.

If the QC is not complete, method returns to 608. If the QC is complete, method 600 proceeds to 648 at FIG. 6B. At 648, method 600 includes repositioning the gantry to the initial rest position when the QC is completed.

Returning to 606, if QC procedure is not in progress, method 600 may proceed to 617. At 617, method 600 includes determining if mammography or biopsy procedure is underway. Determination of whether the x-ray system is currently operating in biopsy or mammography mode may be performed as discussed with respect to FIG. 4 and will not be repeated here for brevity. Briefly, based on one or more accessories detected with the x-ray system, the processor may determine if the x-ray system is operating in biopsy or mammography imaging mode. If biopsy mode is confirmed, method 600 proceeds to 618. At 618, method 600 includes determining if an anesthesia phase is underway. Determining if the anesthesia phase in underway may be based on detecting, with the vision sensors, one or more of presence of anesthesia needle and administration of anesthesia (by monitoring needle insertion in a region of interest). If anesthesia phase is confirmed based on one or more of an object monitoring of the anesthesia needle and a motion monitoring of the anesthesia administration method 600 proceeds to 620 to determine the specific anesthesia step, such as pre-anesthesia phase or post anesthesia phase, etc. based on one or more current anesthesia parameters including anesthesia needle detection, anesthesia administration based on vision sensing of the anesthesia object/action and user input into the workstation user interface. Subsequently, at 624, method 600 includes providing one or more audible instructions to one or more of a patient and a user depending on the stage of anesthesia administration.

Next, method 600 proceeds to 626 to determine if anesthesia administration is complete. Determination of whether the anesthesia phase is complete may be based on detecting one or more anesthesia needle injection into the region of interest and indication by the user via the user interface that the anesthesia phase is completed. If the anesthesia phase is not completed, method 600 continues to monitor the current anesthesia phase and provide audible instructions to one or more of the patient and the user. If the anesthesia phase is complete, method proceeds to 636 at FIG. 6B.

At 636, method 600 includes determining if the biopsy needle has fired (POST-FIRE state). Biopsy needle firing may be detected based on action recognition of biopsy needle firing by vision sensing of needle firing movement with the one or more cameras, or sound sensing of needle firing sound, or a combination thereof.

During this step, in order facilitate faster processing, a frame rate of image acquisition may be increased and a resolution may be decreased. Whereas, during object monitoring, resolution may be increased and frame rate of image acquisition via the vision system cameras may be decreased as clarity of objects is desired. If POST-FIRE state is confirmed, method 600 includes at 638, providing information regarding one or more of completed action (e.g., POST-FIRE image) in the corresponding DICOM image file. If POST-FIRE state is not confirmed, the method may confirm a pre-fire image before writing information regarding current action (e.g., PRE-FIRE image) in DICOM image file. Method then returns to 636 to monitor for the occurrence of a POST-FIRE event.

Returning to 638, upon updating the DICOM image file with the appropriate header, method proceeds to 642 to determine is the procedure is complete. The completion of the procedure may be determined via the vision sensing based on the patient leaving the examination room, for example. If the procedure is complete, the method includes repositioning the gantry to the initial rest state and moving the biopsy bed to the parking position. If the procedure is not complete, the method 600 may continue to monitor the current work flow step and take appropriate actions.

Returning to 618, if anesthesia phase is not detected, method 600 proceeds to determine if the biopsy needle is mounted and a target location for biopsy is selected, or if the biopsy needle is in a PRE-FIRE state. The target location for biopsy may be based on user selecting (e.g., by clicking) the target location on reconstructed images, for example. Biopsy needle mounting may be determined based on vision sensing of the biopsy needle mounted on a holder of the biopsy device. Further, the biopsy needle PRE-FIRE state may also be determined based on vision sensing of the biopsy needle. PRE-FIRE state may indicate that the needle is ready to fire and positioned to extract tissue sample from the body part. PRE-FIRE state may be determined based on absence of needle firing movement, for example. Additionally or alternatively, PRE-FIRE state may be detected based on one or more of position of the biopsy needle with respect to the specimen and acquisition of scout image by the x-ray system prior to firing. If biopsy needle is mounted and a target location for biopsy is selected without anesthesia administration or if PRE-FIRE state is confirmed without anesthesia administration, method 600 proceeds to 630.

At 630, method 600 includes confirming missing anesthesia step, and automatically controlling the biopsy system. This may include, at 632, providing an alert, such as one or more of an audible and a visible alert, to the user, and further includes at 634, inhibiting one or more of image acquisition, movement of needle to pre-fire state, and needle firing (if the needle is already in PRE-FIRE state). In this way, the vision sensor system may be configured to detect a missing step in the workflow.

Returning to 617, if mammography procedure is confirmed, method 600 proceeds to 619. At 619, method 600 includes detecting current mammography imaging step based on one or more of patient position and user position and scan images acquired by the x-ray system. Accordingly, detecting current mammography step may include, at 621, determining one or more current mammography parameters, patient position and user position based on vision sensing of the patient and the user. For example, if the patient is present in the screening area, the processor may determine that the mammography procedure is underway, and if the user is at the workstation (determined based on detecting user presence at the workstation) the processor may determine that the user will acquire an image and the system may provide an audible alert to ask the user to stop breathing. Upon detecting the current mammography step, method 600 proceeds to 623.

At 623, method includes providing one or more audible alerts to one or more of the user and the patient. For example, the processor may provide one or more of indications to the patient to hold breath as discussed above, and indications to the patient regarding the specific work flow step in progress and regarding a percentage of procedure remaining (e.g., procedure 90% complete, etc.).

Next method 600 proceeds to 642 to determine if the procedure is complete as discussed above.

In this way, workflow during quality check, biopsy, and mammography may be continuously monitored by the vision system, and if a missing step is detected, automatic control of the x-ray system may be provided to alert the user and ensure proper procedures are being followed. As a result workflow optimization is achieved.

FIG. 9 shows an exemplary sequence 900 of workflow monitoring during quality check, mammography, and biopsy procedures using a vision system, such as vision system 150 including cameras 151, 152, 153, and 154 at FIG. 1B. In one example, cameras 151 and 152 may be configured as video cameras, and thus, may be utilized for movement monitoring while cameras 153 and 154 may be used for object monitoring. Object monitoring may include accessory monitoring and biopsy device monitoring. Thus in one example, camera 153 may be utilized for accessory monitoring while camera 154 may be used for biopsy device monitoring. Alternatively both cameras 153 and 154 may perform accessory and biopsy device monitoring.

It will be appreciated that embodiments where all four cameras 151, 152, 153, and 154 are utilized for both object and movement monitoring are also within the scope of the disclosure. Further, patient monitoring may be performed by a patient monitoring camera, positioned in the examination room, or by one or more cameras 151, 152, 153, and 154. Workstation monitoring may be performed by a workstation monitoring camera positioned in the examination room. Surrounding object monitoring may be performed by the patient monitoring camera. Thus, in one example, in addition to cameras 151, 152, 153, and 154, a patient monitoring camera which may also be used to monitor surrounding objects, and a workstation camera may be used. In another example, a single fifth camera may be utilized for patient monitoring, surrounding object monitoring and workstation monitoring in addition to cameras 151, 152, 153, and 154.

Although the sequence 900 is discussed with respect to the vision system in FIG. 1B, it will be appreciated that other embodiments of the vision system such as the first vision system of FIG. 1A including cameras 101 and 102, medical vision system 250 at FIG. 2, or vision system 300 at FIG. 3 or any combination thereof can use implemented for workflow monitoring. Specifically, workflow monitoring shown in FIG. 9 may be performed according to an exemplary embodiment of the methods in FIGS. 4A-4B, 5A-5B, and 6A-6B using the vision system discussed herein. Vertical markers t1-t7 represent times of interest during the sequence.

FIG. 9 illustrates an example average acquisition resolution of the vision system for object monitoring at plot 902, average acquisition frame rate of the vision system for movement monitoring at plot 904, average acquisition frame rate of the vision system for object monitoring at plot 908, average acquisition frame rate of the vision system for movement monitoring at plot 910, status of patient monitoring camera at plot 912, status of surrounding object monitoring at plot 914, status of workstation monitoring at plot 916, status of biopsy device monitoring at plot 918, and status of accessory monitoring at plot 920.

The first plot from the top of FIG. 9 is a plot of average acquisition resolution versus time. The Y-axis represents acquisition resolution and the acquisition resolution increases in the direction of Y-axis arrow.

The second plot from the top of FIG. 9 is a plot of average acquisition framerate versus time. The Y-axis represents acquisition framerate and the acquisition framerate increases in the direction of Y-axis arrow.

The third plot from the top of FIG. 9 is a plot of patient monitoring status versus time. In one example, Y-axis represents an ON/OFF status of a patient monitoring camera that monitors patient parameters, including position with respect to one or more of a mammography imaging device and a biopsy device. In another example, the ON/Off indications of the Y-axis refers to status of a first input of the one or more images captured by the patient monitoring camera into a deep learning model. For example, an ON status may indicate that one or more images or image sequences captured by the patient monitoring camera is fed as input into the deep learning model, which is then used for determining one or more of patient position with respect to various components of the mammography system and patient movement out of the examination room. An OFF status may indicate that the one or more images captured by the patient monitoring camera is not used as input for evaluation using the deep learning model. However, the images captured may be stored in non-transitory memory of the mammography system. In yet another example, when patient monitoring is turned OFF, the deep learning model may not utilize patient image data for computation.

The fourth plot from the top of FIG. 9 is a plot of surrounding object monitoring status versus time. In one example, Y-axis represents an ON/OFF status of a surrounding object monitoring camera that monitors presence of one or more surrounding objects including biopsy bed and wheel chair. In another example, the ON/Off indications of the Y-axis refers to a status of a second input of the one or more images captured by surrounding object monitoring camera into the deep learning model. In yet another example, when surrounding object monitoring is turned OFF, the deep learning model may not utilize surrounding object image data for computation.

The fifth plot from the top of FIG. 9 is a plot of workstation monitoring status versus time. In one example, Y-axis represents an ON/OFF status of monitoring of a workstation in communication with a mammography system, including user input regarding operating parameters of a biopsy device and x-ray imaging device. In another example, the ON/Off indications of the Y-axis refers to a status of a third input, including user input (detected by the x-ray system processor) as entered into the workstation interface by the user, into the deep learning model. In yet another example, when workstation monitoring is turned OFF, the deep learning model may not utilize workstation image data for computation.

The sixth plot from the top of FIG. 9 is a plot of biopsy device monitoring status versus time. In one example, Y-axis represents an ON/OFF status of a biopsy device monitoring camera that monitors one or more of biopsy device presence and position. In another example, the ON/Off indications of the Y-axis refers to a status of a fourth input of the one or more images captured by biopsy device monitoring camera into the deep learning model. In yet another example, when biopsy device monitoring is turned OFF, the deep learning model may not utilize biopsy device image data for computation.

The last plot from the top of FIG. 9 is a plot of accessory monitoring status versus time. In one example, Y-axis represents an ON/OFF status of one or more accessory monitoring cameras that monitor one or more accessories associated with the mammography system including biopsy needle, QC phantom, breast spacer, biopsy adaptor, and paddle. In another example, the ON/Off indications of the Y-axis refers to a status of a fifth input of the one or more images captured by accessory monitoring camera into the deep learning model.

At time t0, one or more accessory monitoring cameras may be ON (plot 920) and one or more images from the accessory monitoring camera may be used as input into the deep learning model. Further, at time t0, a user may initiate a quality check procedure. For example, a user may place a QC phantom in a field of view of the mammography system. Using the fifth input from the accessory monitoring camera, the deep learning model may sense the presence of the QC phantom in the field of view, and determine that a quality check procedure is desired. Further, a biopsy device may be positioned relative to the phantom in the field of view, and one or more images from the device monitoring camera may be input in to the deep learning model (plot 918). Using the fourth input from the device monitoring camera, and the fifth input from the one or more accessory monitoring cameras, the deep learning model may determine that a quality check of the mammography system including the biopsy device is desired by the user. Additionally, the user may indicate via an input into a user interface communicating with the mammography system that a QC procedure may be initiated.

Upon determining that the quality check procedure is desired, the deep learning model may activate a quality set up mode for the mammography system. During the quality check set up mode, the workstation monitoring may be turned OFF (plot 916), the surrounding object monitoring may be turned OFF (plot 914), and patient monitoring may be turned OFF (plot 914). Further, acquisition framerate for the object monitoring, acquisition frame rate for action monitoring, and acquisition resolution for action monitoring (plots 908, 910, and 902 respectively) may be lower, and acquisition resolution for the object monitoring (plot 904) may be higher in order to prioritize monitoring of QC phantom and biopsy device during the QC set up mode. Furthermore, the deep learning module may adjust one or more actuators of the mammography system to adjust to the system to set up for the quality check procedure with the biopsy device and phantom in the field of view. For example, adjusting one or more actuators may include rotating gantry to an initial position for quality check and adjusting the scan parameters, including radiation output, commanded voltage of radiation source, and commanded current of radiation source, to conform to QC procedure. Further, during QC set up mode, the deep learning model may actuate a selection of the QC set up mode on the acquisition workstation, and launch a quality check interface.

At t1, the QC set up may be complete. Upon completing the QC set up, the mammography system may output instructions to a user to perform the QC procedure. Between t1 and t2, the user may perform QC procedure. During the QC procedure, the accessory monitoring and the device monitoring may continue to be ON. Further, during the QC procedure, workstation may be monitored (plot 916). Further, as the QC procedure does not involve patient, the surround object monitoring and patient monitoring may be turned off (plots 914 and 912 respectively). During the QC procedure, a type of the QC phantom may be monitored. For example, the deep learning model may determine if the QC phantom in the field of view corresponds to the desired phantom for a biopsy QC procedure. Further, during the QC procedure, a position of the QC phantom with respect to an image receiver plate, orientation of the QC phantom, and positioning of the QC phantom with respect to a pin phantom, may be monitored. Further, during QC testing, the workstation may be monitored to ensure the actual phantom parameters match the parameters entered in the user interface of the mammography system. Furthermore, during the QC testing, one or more audible and visual alerts may be provided to the user if one or more of the type of the QC phantom does not match the desired phantom, orientation of the phantom with respect to a chest wall edge of a bucky of the mammography system, and relative position of the QC phantom with respect to a pin phantom is not within a threshold area. For example, the user may place a flat-field phantom instead of a localization phantom desired for biopsy QC check, or the user may place a phantom that is not optimal for the current mammography system configuration. Accordingly, an audible and/or visual alert indicating that the wrong phantom is used along with recommendations for the desired phantom may be provided to the user. In this way, during the QC procedure, the vision system may continually monitor one or more QC accessories, and the biopsy device, and based on one or more images of the phantom in the field of view of the x-ray system, the deep learning model may determine type, orientation, and position of the phantom with respect to the mammography system, and provide an alert to the user if one or more errors are detected. Furthermore, acquisition resolution and framerate for both action and object monitoring is higher in order to enable more accurate phantom type, orientation and position as discussed above, and also to detect pin firing during a localization accuracy test with a localization phantom to evaluate if the biopsy needle is at the targeted position with respect to the localization phantom, for example.

At t2, the user may complete the QC procedure. Completion of the QC procedure may be determined based on one or more of a user indicating that the procedure is completed via the user interface of the workstation, and the vision system detecting the user removing the QC phantom and the biopsy device.

At t3, the one or more accessory monitoring cameras may continue to be ON (plot 920), the biopsy device monitoring camera may be OFF (plot 918), and the patient monitoring camera may be ON (plot 912). Further at t3, the user may initiate a mammography procedure by placing a patient in a screening space with respect to the x-ray imaging system of the mammography system. Additionally or alternatively, the user may indicate, via the user interface of the workstation that the mammography procedure is desired. The vision system may detect with the patient monitoring camera that the patient is within a screening space of the X-ray system. Additionally, the vision system may detect, with the one or more accessory monitoring cameras, absence of any of the biopsy accessories, including biopsy device, biopsy needle, and biopsy adaptor are not associated with the X-ray system. Further, the one or more accessory monitoring cameras may detect absence of QC-related accessories, such as a QC phantom. In response to detecting patient within the screening area and not detecting biopsy or QC accessories, the deep learning model may determine that a mammography procedure is desired. Further, the deep learning model may use input from the user to confirm if a mammography procedure is desired. Upon confirming that the mammography screening procedure is desired, the deep learning model may initiate monitoring of surrounding objects including wheelchair monitoring (plot 914). At t3, the workstation monitoring may be OFF (plot 916) at t3.

Upon determining that the mammography procedure is desired, between t3 and t4, the deep learning model may automatically set up the mammography system in a mammography mode. Setting up the mammography system based on the vision system to perform the mammography procedure may include adjusting the gantry position to an initial position based on presence of wheelchair. Further, setting up the mammography system may include updating the system speed profile based on presence of surrounding objects such as wheelchair. For example, the deep learning model may adjust the speed profile so to reduce system speed profile to accommodate the presence of wheelchair. Further, between t3 and t4, as mammography procedure does not involve swift actions such as needle firing, acquisition resolution and acquisition frame rate for action monitoring (plots 904 and 910 respectively) is lower. Further, the acquisition framerate for object monitoring (plot 908) is lower. Furthermore, the object monitoring may be performed with higher resolution (plot 902) in order to enable monitoring of one or more accessories used during mammography, such as breast spacers and compression paddle. Further, at some time after t3 and before t4, during the mammography set up, the workstation monitoring may be turned ON in order to ensure that the actual mammography set up and the mammography parameters entered in the workstation interface match. For example, if breast spacer is used to set up the patient for mammography, the workstation interface may be monitored to determine if the workshop interface indicates that the breast spacer is ON. Based on the set up, the acquisition parameters, such as commanded voltage, commanded current, amount of radiation may be adjusted to ensure optimal image quality. Furthermore, gantry position may be fine-tuned for improved image quality based on the presence of one or more accessories. Further still, during mammography set up mode, the deep learning model may actuate a selection of the mammography set up mode on the acquisition workstation and launch a mammography interface.

At t4, the mammography set up may be completed, and between t4 and t5 the mammography procedure may be performed. During the mammography procedure, the accessory monitoring may continue to be ON. However, the biopsy device monitoring may be turned OFF. Further, during the mammography procedure, workstation may continue to be monitored, the surrounding objects, and the patient may continue to be monitored. The mammography procedure may include, compressing a portion of breast with a compression paddle, and upon achieving sufficient immobility of the portion of breast, imaging the portion of breast. Thus, during the mammography procedure, accessory monitoring may include monitoring a change in position of the compression paddle. Further, between t4 and t5, similar to mammography set up mode, acquisition resolution and acquisition frame rate for action monitoring (plots 904 and 910 respectively) is lower. Further, the acquisition framerate for object monitoring (plot 908) is lower. Furthermore, the object monitoring may be performed with higher resolution (plot 902) in order to enable monitoring of one or more accessories used during mammography, such as breast spacers and compression paddle.

At t5, the mammography procedure may be completed. Upon completing the mammography procedure, the images acquired may be stored, and the information regarding the images (e.g., mammography screening image) may be written into the DICOM header. Mammography completion may include an imaging completion phase, a first system reset, patient leaving the screening area, and a second system reset. Imaging completion may be determined by the user via an indication at the user interface. Upon the user indicating that the imaging is completed, a first system reset may be initiated by the mammography system, wherein the mammography system may release the compression paddle, responsive to which, the patient may be moved away from the screening area. The compression paddle resetting to the original position and the patient moving away from the screening area may be detected by the accessory monitoring camera and the patient monitoring camera. Upon confirming imaging completion, the first system reset (that is, compression paddle release), and the patient leaving the screening area, the deep learning model may initiate a second system reset wherein the gantry is returned to its initial position.

After t5, the user may initiate a system transition to perform a biopsy procedure. Accordingly, the user may position a biopsy device at a desired position with respect to the x-ray system. Further, the user may provide an indication via the user interface that the biopsy procedure is desired. The one or more accessory monitoring cameras may continue to capture images and the captured images may be used as input to the deep learning model. Thus, responsive to the biopsy device coupled to the x-ray system, the deep learning model based on input from the one or more accessory monitoring cameras may determine at t6 that a biopsy procedure is desired. Upon confirming that the biopsy procedure is desired, between t6 and t7, biopsy set up mode may be initiated.

Accordingly, between t6 and t7, the biopsy device monitoring may be turned ON. The biopsy device monitoring camera may monitor one or more parameters of the biopsy device including a biopsy needle length of the biopsy needle coupled to the biopsy device, a biopsy device type, biopsy adaptor type and position, and breast spacer presence. Further, upon confirming biopsy procedure, between t6 and t7, surrounding object monitoring may be turned ON and patient monitoring may be turned ON. Thus, the deep learning model, may utilize the one or more accessory monitoring cameras, the device monitoring camera, the surrounding object camera, and the patient monitoring camera to set up the mammography system in the biopsy mode. Setting the biopsy mode may include actuating a selection of the biopsy set up mode on the user interface of the acquisition workstation and launching a biopsy interface on the workstation interface. Further, during biopsy set up, the deep learning model may determine a needle length of the biopsy needle coupled to the biopsy device and determine if the determined needle length (actual needle length) matches with the needle length entered in the user interface of the workstation. If the needle lengths do not match or not within a threshold error range, an alert may be provided to the user. Further, in some embodiments, image acquisition and/or biopsy procedure may not be initiated until the actual needle length matched or is within the threshold error range.

Furthermore, during biopsy set up, the deep learning model may determine if the actual biopsy device type (determined based on input from device monitoring camera) matches the biopsy type selected on the user interface. If the actual and selected biopsy device types do not match, the deep learning model may provide an alert to the user regarding the mismatch error. Additionally, during biopsy set up, a type of approach may be determined by the vision system. For example, the vision system may determine if the biopsy device set up is configured for horizontal approach or vertical approach, and if the paddle type corresponds to the type of approach (horizontal or vertically approach paddle respectively). If the type of biopsy device approach does not match the paddle type, an alert may be provided to the user. In this way, the vision system may be utilized to set-up and check for errors during the set-up. Further during the biopsy set up mode, acquisition frame rate for movement monitoring (plot 910), acquisition frame rate for object monitoring (plot 908), and acquisition resolution for movement monitoring (plot 904) may be lower while the acquisition resolution for object monitoring may be higher (plot 902).

At t7, the biopsy device set up is complete. Next, between t7 and t8, the biopsy procedure is performed. During the biopsy procedure, the accessory monitoring, device monitoring, workstation monitoring, and patient monitoring may be ON. That is, the deep learning module may receive input from the one or more cameras monitoring the mammography system including accessories, device, and patient, and input from the processor regarding user input entered into the workstation interface.

Performing the biopsy procedure includes positioning the patient, either seated or lying down, depending on the type of biopsy procedure prescribed for the patient. Positioning the patient for the biopsy procedure further includes positioning the tissue for extraction by compressing the tissue with the compression paddle. Further, a spacer may be placed beneath the tissue in order to position the tissue with respect to the biopsy needle. The vision system may detect the presence of spacer and may detect the status of spacer indicated on the workstation interface. If the presence or absence of spacer does not match with the corresponding indication of the space status (spacer present or absent) on the workstation interface, an alert may be provided to the user. For example, if the spacer is present on the surface but the workstation interface indicates that the spacer is absent, performing the biopsy procedure may result in the needle entering the spacer instead of the desired region in the tissue. As such, spacer monitoring with the vision system may ensure that the biopsy system is set up with reduced error so as to improve efficiency and accuracy of the biopsy procedure.

Upon positioning the patient, anesthesia is administered. The vision system may monitor work flow steps, including monitoring administration of anesthesia, during the biopsy procedure. For example, the deep learning module, using input from the vision system, may monitor if anesthesia needle is inserted into the area of interest. Further, the deep learning module, using input from the vision system, may monitor if the workstation interface confirms anesthesia administration. Until anesthesia administration is confirmed, tissue extraction with the biopsy device may not be permitted. Further, if an attempt is made to extract the tissue without anesthesia, an alert may be provided to the user indicating that the anesthesia step has not been performed or completed.

Further, during the biopsy procedure, the deep learning module with the inputs from the vision system may monitor position of the needle. Specifically, inputs from the vision system may be used to monitor biopsy needle movement, and based on the needle movement and position, the deep learning module may determine different workflow stages of biopsy including a PRE-FIRE stage before the biopsy needle firing, and a POST-FIRE stage after biopsy needle entering and exiting the tissue. In order to achieve improved movement and object monitoring, acquisition frame rate for movement monitoring (plot 910), and acquisition resolution for both object and movement monitoring may be increased (plots 902 and 904) while the acquisition frame rate for object monitoring (plot 908) may be decreased. Beyond t8, patient monitoring may be continued until the patient exits the examination room.

In this way, by vision sensing, workflow for the x-ray system may be monitored, and the system operation may be adjusted and indications may be provided to the user based on the vision sensing to improve efficiency of workflow during mammography, biopsy, and quality check procedures.

The technical effect of using vision system to detect specific accessories and work flow steps is increased range of monitoring of various accessories and components of the mammography system without reliance on hardware sensors. Another technical effect of using vision system to detect specific accessories and work flow steps is improved workflow efficiency. Yet another technical effect of monitoring accessories with respect to workflow steps is mitigation of user error during each of the procedures performed with the x-ray mammography system, which improves patient care and comfort.

An embodiment for a method for an x-ray mammography system includes determining, via vision sensing using one or more cameras coupled to the x-ray mammography system, a current workflow in a current mode of the x-ray mammography system; and adjusting one or more inputs into a user interface of the mammography system during a set-up portion of the current workflow; wherein the vision sensing using one or more cameras includes one or more of monitoring one or more accessories coupled to the x-ray mammography system and one or more actions during the current mode. A first example of the method includes wherein the one or more accessories includes one or more of biopsy device, a breast spacer, and a biopsy paddle; wherein determining the current mode includes determining a biopsy mode in response to detecting one or more of the biopsy device, the breast spacer, and the biopsy paddle via the vision sensing; wherein adjusting the one or more inputs includes launching a biopsy mode interface on the user interface coupled to the x-ray mammography system, and selecting one or more of a biopsy exam type and a type of biopsy device detected on the launched biopsy mode interface, in response to detecting one or more of the biopsy device and the breast spacer via the vision sensing. In a second example of the method, which optionally includes the first example, and further includes wherein the one or more accessories includes a quality check phantom; wherein determining the current mode includes determining a quality check mode in response to detecting the quality check phantom; and wherein adjusting the one or more inputs includes launching a quality check interface on the user interface in response to detecting the quality check phantom. In a third example of the method, which optionally includes one or both of the first and second examples, the method further includes wherein the one or more inputs includes selecting breast spacer presence on the launched biopsy mode interface in response to detecting the breast spacer via the vision sensing, and selecting breast spacer absence in response to not detecting the breast spacer via the vision sensing. In a fourth example of the method, which optionally includes one or more or each of the first through third examples, the method further includes during the current mode, after the set-up portion of the current workflow, obtaining one or more medical scan images with the x-ray mammography system; and updating a portion of image data of the one or more medical scan images based on the one or more actions. In a fifth example of the method, which optionally includes one or more or each of the first through fourth examples, the method further includes wherein the current mode is a biopsy mode; and wherein the one or more actions include one or more of a biopsy needle firing movement and administration of anesthesia. In a sixth example of the method, which optionally includes one or more or each of the first through fifth examples, the method includes detecting a different accessory and one or more associated accessory characteristics via vision sensing using the one or more cameras after the set-up is complete and while operating the x-ray mammography system in the current mode; detecting one or more user inputs corresponding to the different accessory and the one or more associated accessory characteristics on the user interface; and indicating an error on the user interface in response to the one or more user inputs not matching with the detected different accessory and the one or more associated accessory characteristics. In a seventh example of the method, which optionally includes one or more or each of the first through sixth examples, the method further includes inhibiting a next step in the operation of the x-ray mammography system in the current mode in response to the one or more user inputs not matching the detected different accessory; and wherein the next step includes one or more of obtaining one or more medical scan images and firing a biopsy needle. In an eighth example of the method, which optionally includes one or more or each of the first through seventh examples, the method further includes wherein the different accessory is a biopsy needle and the corresponding different accessory characteristics is one or more of a needle length and an associated biopsy device type. In an ninth example of the method, which optionally includes one or more or each of the first through eighth examples, the method further includes wherein the different accessory is a breast spacer and the associated accessory characteristic is the presence of the breast spacer in response to detecting the breast spacer; and wherein the one or more user inputs include a selection of a status of presence of the breast spacer on the user interface.

An embodiment is directed to a method for monitoring a mammography system comprising: monitoring, via a computer vision system, a workflow step during the operation of the mammography system; and in response to not detecting the workflow step, inhibiting a subsequent workflow step, and providing an alert to the user regarding the workflow step; wherein monitoring the workflow step includes monitoring one or more of one or more accessories present in an imaging volume of the mammography system, a biopsy device coupled to the mammography system, one or more surrounding objects within a screening area of the mammography system, one or more actions including user action and device action, and one or more user inputs entered into a user interface of the mammography system. A first example of the method includes wherein the workflow step includes administration of anesthesia; and wherein the subsequent workflow step includes inhibiting one or more of a movement of a biopsy needle and image acquisition with the mammography system. In a second example of the method, which optionally includes the first example, and further includes during set-up of the mammography system prior to operating the mammography system, adjusting one or more of a status of the mammography system on the user interface based on identifying one or more of the one or more accessories present in the imaging volume of the mammography system, the biopsy device coupled to the mammography system, and the one or more surrounding objects within the screening area of the mammography system; and wherein the computer vision system includes one or more cameras coupled to the mammography system and one or more cameras monitoring the exam room. In a third example of the method, which optionally includes one or both of the first and second examples, and further includes adjusting the status of the mammography system to a quality check mode in response to the one or more accessories including a quality check phantom; adjusting the status of the mammography system to a biopsy mode in response to identifying the biopsy device, and the one or more accessories including one or more of a breast spacer and a biopsy needle; and adjusting the status of the mammography system to a mammography mode in response to not detecting any of the one or more quality check phantom, the biopsy device, and the biopsy accessories. In a fourth example of the method, which optionally includes one or more or each of the first through third examples, the method further includes indicating one or more errors in response to the one or more user inputs on the user interface not corresponding to the one or more of the accessories and the biopsy device; and inhibiting a next step in response to the one or more user inputs on the user interface not corresponding to the one or more of the accessories, and the biopsy device. In a fifth example of the method, which optionally includes one or more or each of the first through fourth examples, the method further includes wherein indicating one or more errors includes indicating a potential needle collision with a biopsy spacer when the one or more user inputs indicates absence of the spacer while the biopsy spacer is identified in the imaging volume of the mammography system. In a sixth example of the method, which optionally includes one or more or each of the first through fifth examples, the method includes indicating one or more errors includes indicating one or more of a phantom type error and phantom orientation error based on one or more of positioning of a phantom detected in the imaging volume and one or more user inputs indicating a phantom type.

An embodiment for a system for workflow monitoring in medical imaging is provided. The system includes a gantry including a radiation source for emitting radiation rays, a detector for receiving the radiation rays, and a collimator for adjusting a field of view; a vision sensor system including one or more cameras; and a workstation communicatively coupled to the gantry and including a user interface and a processor, the user interface including a display portion, and the processor configured with instructions in non-transitory memory that when executed cause the processor to: detect, with the vision sensor system, one or more accessories of the imaging system; and adjust one or more of a position of the gantry and further adjust an indication of an operating status of the imaging system on the user interface based on the one or more accessories detected. In a first example of the system, the processor further includes instructions to detect, with the vision system, one or more surrounding objects within a threshold screening area of the imaging system; and adjust a system speed profile based on the one or more surrounding objects detected; wherein the one or more surrounding objects include a wheelchair. In a second example of the imaging system, which optionally includes the first example, the vision system includes one or more of an optical camera, wide-angle optical camera, and a depth camera.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method executable by an image processing system an x-ray mammography system, the method comprising:
    determining, with the image processing system via vision sensing using one or more cameras of the x-ray mammography system, a current mode of the x-ray mammography system and a current workflow of the current mode; and
    automatically adjusting, with the image processing system, one or more inputs into a user interface of the x-ray mammography system during a set-up portion of the current workflow based on the current mode and the current workflow as determined via the vision sensing;
    wherein the vision sensing using one or more cameras includes one or more of monitoring one or more accessories coupled to the x-ray mammography system and one or more actions during the current mode.

2. The method of claim 1, wherein the one or more accessories includes one or more of biopsy device, a breast spacer, and a biopsy paddle; wherein determining the current mode includes determining a biopsy mode in response to detecting one or more of the biopsy device, the breast spacer, and the biopsy paddle via the vision sensing; wherein adjusting the one or more inputs includes launching a biopsy mode interface on the user interface, and selecting one or more of a biopsy exam type and a type of biopsy device detected on the launched biopsy mode interface, in response to detecting one or more of the biopsy device and the breast spacer via the vision sensing, and wherein the user interface includes a display portion.

3. The method of claim 2, wherein the one or more inputs includes selecting breast spacer presence on the launched biopsy mode interface in response to detecting the breast spacer via the vision sensing, and selecting breast spacer absence in response to not detecting the breast spacer via the vision sensing.

4. The method of claim 1, wherein the one or more accessories includes a quality check phantom; wherein determining the current mode includes determining a quality check mode in response to detecting the quality check phantom; and wherein adjusting the one or more inputs includes launching a quality check interface on the user interface in response to detecting the quality check phantom.

5. The method of claim 1, further comprising:
    during the current mode,
        after the set-up portion of the current workflow, obtaining one or more medical scan images with the x-ray mammography system; and
        updating a portion of image data of the one or more medical scan images based on the one or more actions.

6. The method of claim 5, wherein the current mode is a biopsy mode; and wherein the one or more actions include one or more of a biopsy needle firing movement and administration of anesthesia.

7. The method of claim 1, further comprising:
    detecting a different accessory and one or more associated accessory characteristics via vision sensing using the one or more cameras after the set-up portion is complete and while operating the x-ray mammography system in the current mode;
    detecting one or more user inputs corresponding to the different accessory and the one or more associated accessory characteristics on the user interface; and
    indicating an error on the user interface in response to the one or more user inputs not matching with the detected different accessory and the one or more associated accessory characteristics.

8. The method of claim 7, further comprising:
    inhibiting a next step in the operation of the x-ray mammography system in the current mode in response to the one or more user inputs not matching the detected different accessory; and
    wherein the next step includes one or more of obtaining one or more medical scan images and firing a biopsy needle.

9. The method of claim 8, wherein the different accessory is a biopsy needle and the corresponding different accessory characteristics is one or more of a needle length and an associated biopsy device type.

10. The method of claim 8, wherein the different accessory is a breast spacer and the associated accessory characteristic is the presence of the breast spacer in response to detecting the breast spacer; and wherein the one or more user inputs include a selection of a status of presence of the breast spacer on the user interface.

11. A method for monitoring a mammography system comprising:
    monitoring, via a computer vision system, a workflow step during the operation of the mammography system; and
    in response to not detecting the workflow step, inhibiting a subsequent workflow step, and providing an alert to the user regarding the workflow step;
    wherein monitoring the workflow step includes monitoring one or more of one or more accessories present in an imaging volume of the mammography system, a biopsy device coupled to the mammography system, one or more surrounding objects within a screening area of the mammography system, one or more actions including user action and device action, and one or more user inputs entered into a user interface of the mammography system.

12. The method of claim 11, wherein the workflow step includes administration of anesthesia; and wherein the subsequent workflow step includes inhibiting one or more of a movement of a biopsy needle and image acquisition with the mammography system.

13. The method of claim 11, further comprising:
    during set-up of the mammography system prior to operating the mammography system, adjusting one or more of a status of the mammography system on the user interface based on identifying one or more of the one or more accessories present in the imaging volume of the mammography system, the biopsy device coupled to the mammography system, and the one or more surrounding objects within the screening area of the mammography system; and wherein the computer vision system includes one or more cameras coupled to the mammography system and one or more cameras monitoring the exam room.

14. The method of claim 13, further comprising:
adjusting the status of the mammography system to a quality check mode in response to the one or more accessories including a quality check phantom;
adjusting the status of the mammography system to a biopsy mode in response to identifying the biopsy device, and the one or more accessories including one or more of a breast spacer and a biopsy needle; and
adjusting the status of the mammography system to a mammography mode in response to not detecting any of the one or more quality check phantom, the biopsy device, and the biopsy accessories.

15. The method of claim 11, further comprising:
indicating one or more errors in response to the one or more user inputs on the user interface not corresponding to the one or more of the accessories and the biopsy device; and inhibiting a next step in response to the one or more user inputs on the user interface not corresponding to the one or more of the accessories, and the biopsy device.

16. The method of claim 15, wherein indicating one or more errors includes indicating a potential needle collision with a biopsy spacer when the one or more user inputs indicates absence of the spacer while the biopsy spacer is identified in the imaging volume of the mammography system.

17. The method of claim 15, wherein indicating one or more errors includes indicating one or more of a phantom type error and phantom orientation error based on one or more of positioning of a phantom detected in the imaging volume and one or more user inputs indicating a phantom type.

18. The system of claim 17, wherein the vision system includes one or more of an optical camera, wide-angle optical camera, and a depth camera.

19. A medical imaging system, comprising:
a gantry including a radiation source for emitting radiation rays, a detector for receiving the radiation rays, and a collimator for adjusting a field of view;
a vision sensor system including one or more cameras; and
a workstation communicatively coupled to the gantry and including a user interface and a processor, the user interface including a display portion, and the processor configured with instructions in non-transitory memory that when executed cause the processor to:
detect, with the vision sensor system, one or more accessories of the imaging system; and
adjust a position of the gantry based on the one or more accessories detected and further adjust an indication of an operating status of the imaging system on the user interface based on the one or more accessories detected.

20. The system of claim 19, wherein the processor further includes instructions to:
detect, with the vision system, one or more surrounding objects within a threshold screening area of the imaging system; and
adjust a system speed profile based on the one or more surrounding objects detected;
wherein the one or more surrounding objects include a wheelchair.

* * * * *